(12) United States Patent
Dao et al.

(10) Patent No.: US 10,245,286 B2
(45) Date of Patent: Apr. 2, 2019

(54) METHODS AND COMPOSITIONS FOR MODULATING ANGIOGENESIS AND VASCULOGENESIS

(71) Applicant: SanBio, Inc., Mountain View, CA (US)

(72) Inventors: Monique Dao, Huntington Beach, CA (US); Ciara Tate, Chicago, IL (US); Casey C. Case, San Mateo, CA (US)

(73) Assignee: SanBio, Inc., Mountain View, CA (US)

( * ) Notice: Subject to any disclaimer, the term of this patent is extended or adjusted under 35 U.S.C. 154(b) by 0 days.

(21) Appl. No.: 15/608,656

(22) Filed: May 30, 2017

(65) Prior Publication Data

US 2017/0258850 A1     Sep. 14, 2017

Related U.S. Application Data

(63) Continuation of application No. 15/063,290, filed on Mar. 7, 2016, now abandoned, which is a continuation of application No. 13/750,772, filed on Jan. 25, 2013, now abandoned.

(60) Provisional application No. 61/591,486, filed on Jan. 27, 2012, provisional application No. 61/637,740, filed on Apr. 24, 2012, provisional application No. 61/709,619, filed on Oct. 4, 2012.

(51) Int. Cl.
| | |
|---|---|
| *A61K 48/00* | (2006.01) |
| *A61K 35/28* | (2015.01) |
| *C12N 5/071* | (2010.01) |
| *A61K 35/34* | (2015.01) |
| *A61K 38/18* | (2006.01) |
| *A61K 45/06* | (2006.01) |
| *C12N 5/0775* | (2010.01) |
| *A61K 35/44* | (2015.01) |
| *A61L 27/38* | (2006.01) |

(52) U.S. Cl.
CPC .............. *A61K 35/34* (2013.01); *A61K 35/28* (2013.01); *A61K 35/44* (2013.01); *A61K 38/1866* (2013.01); *A61K 45/06* (2013.01); *A61L 27/3834* (2013.01); *C12N 5/0662* (2013.01); *C12N 5/0663* (2013.01); *C12N 5/0668* (2013.01); *C12N 5/0697* (2013.01); *A61K 48/00* (2013.01); *C12N 2501/42* (2013.01); *C12N 2502/1347* (2013.01); *C12N 2502/28* (2013.01); *C12N 2510/02* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 6,989,271 B2 | 1/2006 | Dezawa et al. | |
| 7,026,462 B2 | 4/2006 | Rebar et al. | |
| 7,067,317 B2 | 6/2006 | Rebar et al. | |
| 7,560,440 B2 | 7/2009 | Rebar et al. | |
| 7,605,140 B2 | 10/2009 | Rebar et al. | |
| 7,682,825 B2 | 3/2010 | Dezawa et al. | |
| 8,071,564 B2 | 12/2011 | Rebar et al. | |
| 8,092,792 B2 | 1/2012 | Dezawa et al. | |
| 8,133,725 B2 | 3/2012 | Dezawa et al. | |
| 8,361,456 B2 | 1/2013 | Dezawa et al. | |
| 8,785,190 B2 | 7/2014 | Dao et al. | |
| 8,945,919 B2 | 2/2015 | Mori et al. | |
| 9,566,135 B2 | 2/2017 | Elia | |
| 2005/0267062 A1 | 12/2005 | Rebar et al. | |
| 2006/0051334 A1 | 3/2006 | Kornowski et al. | |
| 2006/0216276 A1 | 9/2006 | Dezawa et al. | |
| 2006/0251624 A1 | 11/2006 | Dezawa | |
| 2008/0095709 A1 | 4/2008 | Ella | |
| 2010/0266554 A1 | 10/2010 | Mori et al. | |
| 2010/0310529 A1 | 12/2010 | Aizman | |
| 2011/0136114 A1 | 6/2011 | Case | |
| 2011/0165131 A1 | 7/2011 | Elia | |
| 2011/0306137 A1 | 12/2011 | Aizman | |
| 2012/0263681 A1 | 10/2012 | Miyoshi et al. | |
| 2013/0071924 A1 | 3/2013 | Dezawa | |
| 2013/0095084 A1 | 4/2013 | Dao et al. | |
| 2013/0195817 A1 | 8/2013 | Dao et al. | |
| 2013/0210000 A1 | 8/2013 | Aizman et al. | |
| 2014/0286918 A1 | 9/2014 | Dao et al. | |
| 2014/0363408 A1 | 12/2014 | Aizman | |
| 2016/0263159 A1 | 9/2016 | Dao et al. | |

FOREIGN PATENT DOCUMENTS

| | | |
|---|---|---|
| AU | 2009200996 | 4/2009 |
| WO | WO 2002/046412 | 6/2002 |
| WO | WO 2006/096640 | 9/2006 |
| WO | WO 2008/010246 | 1/2008 |
| WO | WO 2008/102460 | 8/2008 |

(Continued)

OTHER PUBLICATIONS

Li et al., Circulation. Mar. 1, 2011;123(8):866-876 (Year: 2011).*
Aizman et al., "Extracellular Matrix Produced by Bone Marrow Stromal Cells and by Their Derivatne, SB623 Cells, Supports Neural Cell Growth," J Neurosci. Res. 87(14):3198-3206 (2009).
Ali et al., "Notch-Induced Human Bone Marrow Stromal Cell Grafts Express Neuronal Phenotypic Markers and Reduce Ischemic Cell Loss in Tandem With Behavioral Recovery of Transplanted Stroke Animals," Cell Transplantation, 17:458 (2008).
Dao, et al., "Comparing the Angiogenic Potency of Naive Marrow Stromal Cells and Notch-Transfected Marrow Stromal Cells," J Translational Medicine, 11:81-91 (2013).

(Continued)

*Primary Examiner* — Daniel C Gamett
(74) *Attorney, Agent, or Firm* — Levine Bagade Han LLP

(57) ABSTRACT

Disclosed herein are methods and compositions for stimulating angiogenesis, using cells descended from marrow adherent stromal cells that have been transfected with sequences encoding a Notch intracellular domain. Applications of these methods and compositions include treatment of ischemic disorders such as stroke.

21 Claims, 10 Drawing Sheets

(56) References Cited

FOREIGN PATENT DOCUMENTS

WO    WO 2013/112917    8/2013

OTHER PUBLICATIONS

Dao et al., "Comparing the Immunosuppressive Potency of Naive Marrow Stromal Cells and Notch-Transfected Marrow Stromal Cells," J Neuroinflammation, 8:133-146 (2011).

Dezawa et al. "Sciatic Nerve Regeneration in Rats Induced by Transplantation of In Vitro Differentiated Bone-Marrow Stromal Cells," The European Journal of Neuroscience 14(11):1771-1776 (2001).

Dezawa et al., "Transdifferentiation of Bone Marrow Stromal Cells to Neural Cells and Application to Stem Cell Therapy," Acta Anatomica Nipponica 78suppl:97 (Abstract S04-6) (2003) (English translation also enclosed).

Dezawa et al., "Treatment of Neurodegenerative Diseases Using Adult Bone Marrow Stromal Cell-Derived Neurons," Expert Opinion on Biological Therapy 5(4):427-435 (2005).

Dezawa, et al., "Specific Induction of Neuronal Cells From Bone Marrow Stromal Cells and Application for Autologous Transplantation," J Clin Invest 113(12):1701-1710 (2004).

Glavaski-Joksimovic, et al., "Reversal of Dopaminergic Degeneration in a Parkinsonian Rat Following Micrografting of Human Bone Marrow-Derived Neural Progenitors," Cell Transplant 18:801-814 (2009).

Greenberg et al., "A Role for VEGF as a Negative Regula Tor of Pericyte Function and Vessel Maturation," Nature, 456:809-813 (2008).

Harvey et al., "Proteomic Analysis of the Extracellular Matrix Produced by Mesenchymal Stromal Cells: Implications for Cell Therapy Mechanism," PLOS ONE, 8(11):e79283, Nov. 2013.

Reynolds, "Potrntial Relevance of Bell-Shaped and U-Shaped Dose-Responses for the Therapeutic Targeting of Angiogensis in Cancer," International Dose-Response Society, 8:253-284. (2010).

Tajiri et al., "Stem Cell Recruitment of Newly Formed Host Cells Via a Successful Seduction? Filling the Gap Between Neurogenic Niche and Injured Brain Site," PLOS ONE, 8(9):e74857 (2013).

Tate et al. "Transplanted Mesenchymal Stem Cells Aid the Injured Brain through Trophic Support Mechanisms," Stem Cells and Cancer Stem Cells. vol. 4, M.A. Hayat (Ed), 297-304 (2012).

Tate et al., "Human Mesenchymal Stromal Cells and Their Derivative, S8623 Cells, Rescue Neural Cells via Trophic Support Following In Vitro Ischemia," Cell Transplantation, vol. 19, pp. 973-984, 2010.

Tate et al., "Moving Cell Therapy From Basic Research Into the Clinic: SB623 Cells for Stroke Disability," Cell Transplantation, 20:588 (2011).

Tate et al., "Mesenchymal Stromal Cells to Treat Brain Injury," Advanced Topics in Neurological Disorders, K. S. Chen (Ed), 45-78 (2012).

Visse et al., "Matrix Metalloproteinases and Tissue Inhibitors of Metalloproteinases, Structure, Function, and Biochemistry", Circulation Research, 92:827-839 (2003).

Wu et al., Stem Cells, 25(10):2648-2659, Oct. 2007.

Xu et al., "Transplantation of Neuronal Cells Induced From Human Mesenchymal Stem Cells Improves Neurological Functions Afterstroke Without Cell Fusion," J. Neuroscience Research 88:3598-3609 (2010).

Yang, J P et al., "The dose-effectiveness of intranasal VEGF in treatment of experimental stroke," Neuroscience Letters, 461(3): 212-216, Sep. 15, 2009.

Yasuhara, et al., "Notch-Induced Rat and Human Bone Marrow Stromal Cell Grafts Reduce Ischemic Cell Loss and Ameliorate Behavioral Deficits in Chronic Stroke Animals," Stem Cells and Development 18:1501-1514 (2009).

Tate, C. C. et al., "SB623 Cells Promote Angiogenesis—A Potential Mechanism of Action ofr Enhancing Neural Regeneration," Cell Transplant, vol. 21, Suppl. 1, p. 794 (Apr. 2012).

* cited by examiner

MSC     SB623     OptiMEM

METHODS AND COMPOSITIONS FOR MODULATING ANGIOGENESIS AND VASCULOGENESIS

CROSS REFERENCE TO RELATED APPLICATIONS

This application is a continuation of U.S. patent application Ser. No. 15/063,290 filed Mar. 7, 2016 which is a continuation of U.S. patent application Ser. No. 13/750,772 filed Jan. 25, 2013 which claims the benefit of U.S. Provisional Patent Application No. 61/591,486 filed on Jan. 27, 2012, U.S. Provisional Patent Application No. 61/637,740 filed on Apr. 24, 2012, and U.S. Provisional Patent Application No. 61/709,619 filed on Oct. 4, 2012. The specifications and drawings of all of the aforementioned applications are incorporated herein by reference in then entireties for all purposes.

STATEMENT REGARDING FEDERAL SUPPORT

Not applicable.

FIELD

The present disclosure is in the fields of angiogenesis and vasculogenesis; e.g., for the treatment of ischemic events such as stroke. It is also in the field of stem cells and cells derived from stem cells by genetic manipulation.

BACKGROUND

In stable stroke, reinstating vascular flow is imperative for restoring nutrient supply in the brain. To repair vascular damage after prolonged ischemia at least two sequential steps are needed. The first step is angiogenic sprouting of endothelial cells (ECs); this process entails the initial proliferation of endothelial cells and remodeling of the surrounding extracellular matrix. VEGF-mediated prolifdation of ECs and matrix metalloproteinases are among the major components of angiogenic sprouting. The second step is vessel stabilization; a process that relies on recruitment of vascular smooth muscle cells to encase the young vessels. Monocytes and pericytes are also involved in vessel stabilization, producing the appropriate arteriogenic factors and extracellular matrix proteins. In the absence of vessel stabilization by smooth muscle cells and pericytes, regression of nascent vasculature can occur.

Marrow stromal cells (MSCs, also known as mesenchymal stem cells)) have been shown to promote revascularization after cerebral artery occlusion and traumatic brain injury. Omori et al. (2008) *Brain Res.* 1236:30-38; Onda et al. (2008) *J. Cereb. Blood Flow Metab.* 28:329-340; Pavlichenko et al. (2008) *Brain Res.* 1233:203-213; Xiong et al.(2009) *Brain Res.* 1263:183-191. SB623 cells are a derivative of marrow stromal cells, obtained by transfecting marrow stromal cells with a vector containing sequences encoding a Notch intracellular domain (NICD). See, for example, U.S. Pat. No. 7,682,825 and Dezawa et al. (2004) *J. Clin. Investig.* 13:1701-1710. SB623 cells elicit functional improvement in experimental stroke models. See, for example, U.S. Pat. No. 8,092,792 and Yasuhara et al. (2009) *Stem Cells and Development* 18:1501-1514. Although the secretome of SB623 cells is comparable to that of the parental MSCs; different levels of specific trophic factors have been observed to be secreted by MSCs, as compared to SB623 cells. See, for example, Tate et al. (2010) *Cell Transplantation* 19:973-984; U.S. Patent Application Publication No. 2010/0266554. Moreover, many of the factors whose expression levels differ between MSCs and SB623 cells have been reported to be involved in vascular regeneration.

Because stroke is a leading cause of adult disability in the United States, and is the second leading cause of death worldwide, there remains a need for treatments to restore blood supply to, and promote reperfusion of, regions of stroke-induced ischemic damage in the brain.

SUMMARY

The present inventors have discovered that descendents of mesenchymal stein cells that have been transfected with sequences encoding a Notch intracellular domain (i.e. SB623 cells) have the surprising property of being able to synthesize and secrete factors that promote angiogenesis. Because angiogenesis, i.e., the formation of new blood vessels, is a critical part of the endogenous repair process in brain injury and disease, this discovery provides new methods of treatment for vascular disorders such as stroke.

Accordingly, the present disclosure provides, inter alia:

1. A method for augmenting angiogenesis in a subject, the method comprising administering to the subject a population of SB623 cells; wherein the SB623 cells, are obtained by (a) providing a culture of mesenchymal stem cells, (b) contacting the cell culture of step (a) with a polynucleotide comprising sequences encoding a Notch intracellular domain (NICD) wherein said polynucleotide does not encode a full-length Notch protein, (c) selecting cells that comprise the polynucleotide of step (b), and (d) further culturing the selected cells of step (c) in the absence of selection.

2. The method of embodiment 1, wherein the augmentation of angiogenesis occurs in the central nervous system.

3. The method of embodiment 2, wherein the augmentation of angiogenesis occurs in the brain.

4. A method for repairing ischemic damage in a subject, the method comprising administering to the subject a population of SB623 cells; wherein the SB623 cells are obtained by (a) providing a culture of mesenchymal stem cells, (b) contacting the cell culture of step (a) with a polynucleotide comprising sequences encoding a Notch intracellular domain (NICD) wherein said polynucleotide does not encode a full-length Notch protein, (c) selecting cells that comprise the polynucleotide of step (b), and (d) further culturing the selected cells of step (c) in the absence of selection.

5. The method of embodiment 4, wherein the ischemic damage occurs in the central nervous system.

6. The method of embodiment 5, wherein the ischemic damage occurs in the brain.

7. The method of embodiment 6, wherein the ischemic damage results from stroke.

8. A method for enhancing survival of endothelial cells, the method comprising contacting the endothelial cells with a population of SB623 cells; wherein the SB623 cells are obtained by (a) providing a culture of mesenchymal stem cells, (b) contacting the cell culture of step (a) with a polynucleotide comprising sequences encoding a Notch intracellular domain (NICD) wherein said polynucleotide does not encode a full-length Notch protein, (c) selecting cells that comprise the polynucleotide of step (b), and (d) further culturing the selected cells of step (c) in the absence of selection.

9. The method of embodiment 8, wherein the method prevents the death of endothelial cells.

10. The method of either of embodiments 8 or 9, wherein the endothelial cells are in a subject.

11. The method of embodiment 10, wherein the endothelial cells are in he central nervous system of the subject.

12. The method of embodiment 11, wherein the endothelial cells are in the brain of the subject.

13. A method for stimulating proliferation of endothelial cells, the method comprising contacting the endothelial cells with a population of SB623 cells; wherein the SB623 cells are obtained by (a) providing a culture of mesenchymal stem cells, (b) contacting the cell culture of step (a) with a polynucleotide comprising sequences encoding a Notch intracellular domain (NICD) wherein said polynucleotide does not encode a full-length Notch protein, (c) selecting cells that comprise the polynucleotide of step (b), and (d) further culturing the selected cells of step (c) in the absence of selection.

14. The method of embodiment 13, wherein the endothelial cells are in a subject.

15. The method of embodiment 14, wherein the endothelial cells are in the central nervous system of the subject.

16. The method of embodiment 15, wherein the endothelial cells are in the brain of the subject.

17. A method for enhancing the branching of blood vessels, the method comprising contacting the vessels with a population of SB623 cells wherein the SB623 cells are obtained by (a) providing a culture of mesenchymal stem cells, (b) contacting the cell culture of step (a) with a polynucleotide comprising sequences encoding a Notch intracellular domain (NICD) wherein said polynucleotide does not encode a full-length Notch protein, (c) selecting cells that comprise the polynucleotide of step (b), and (d) further culturing the selected cells of step (c) in the absence of selection.

18. The method of embodiment 17, wherein the blood vessels are in a subject

19. The method of embodiment 18, wherein the blood vessels are in the central nervous system of the subject.

20. The method of embodiment 19, wherein the blood vessels are in the brain of the subject.

21. A method for augmenting angiogenesis in a subject, the method comprising administering to the subject (1) a population of SB623 cells; wherein the SB623 cells are obtained by (a) providing a culture of mesenchymal stem cells, (b) contacting the cell culture of step (a) with a polynucleotide comprising sequences encoding a Notch intracellular domain (NICD) wherein said polynucleotide does not encode a full-length Notch protein, (c) selecting cells that comprise the polynucleotide of step (b), and (d) further culturing the selected cells of step (c) in the absence of selection; and (2) a pro-angiogenic agent.

22. The method of embodiment 21, wherein the augmentation of angiogenesis occurs in the central nervous system.

23. The method of embodiment 22, wherein the augmentation f angiogenesis occurs in the brain.

24. The method of embodiment 21, wherein the pro-angiogenic agent is a nucleic acid.

25. The method of embodiment 21, wherein the pro-angiogenic agent is a polypeptide.

26. The method of embodiment 25, wherein the polypeptide is a transcription factor that activates expression of a pro-angiogenic protein.

27. The method of embodiment 26, wherein the pro-angiogenic protein is vascular endothelial growth factor (VEGF).

28. The method of embodiment 27, wherein the transcription factor is a non-naturally-occurring zinc finger protein that activates transcription of the VEGF gene.

29. A method for repairing ischemic damage in a subject, the method comprising administering to the subject (1) a population of SB623 cells; wherein the SB623 cells are obtained by (a) providing a culture of mesenchymal stem cells, (b) contacting the cell culture of step (a) with a polynucleotide comprising sequences encoding a Notch intracellular domain (NICD) wherein said polynucleotide does not encode a full-length Notch protein, (c) selecting cells that comprise the polynucleotide of step (b), and (d) further culturing the selected cells of step (c) in the absence of selection; and (2) a pro-angiogenic agent.

30. The method of embodiment 29, wherein the ischemic damage occurs in the central nervous system.

31. The method of embodiment 30, wherein the ischemic damage occurs in the brain.

32. The method of embodiment 31, wherein the ischemic damage results from stroke.

33. The method of embodiment 29, wherein the pro-angiogenic agent is a nucleic acid.

34. The method of embodiment 29, wherein the pro-angiogenic agent is a polypeptide.

35. The method of embodiment 34, wherein the polypeptide is a transcription factor that activates expression of a pro-angiogenic protein.

36. The method of embodiment 35, wherein the pro-angiogenic protein is vascular endothelial growth factor (VEGF).

37. The method of embodiment 36, wherein the transcription factor is a non-naturally-occurring zinc finger protein that activates transcription of the VEGF gene.

38. A method for treating stroke in a subject, the method comprising administering to the subject (1) a population of SB23 cells; wherein the SB623 cells are obtained by (a) providing a culture of mesenchymal stem cells, (b) contacting the cell culture of step (a) with a polynucleotide comprising sequences encoding a Notch intracellular domain (NICD) wherein said polynucleotide does not encode a full-length Notch protein, (c) selecting cells that comprise the polynucleotide of step (b), and (d) further culturing the selected cells of step (c) in the absence of selection; and (2) a pro-angiogenic agent.

39. The method of embodiment 38, wherein the pro-angiogenic agent is a nucleic acid.

40. The method of embodiment 38, wherein the pro-angiogenic agent is a polypeptide.

41. The method of embodiment 40, wherein the polypeptide is a transcription factor that activates expression of a pro-angiogenic protein.

42. The method of embodiment 41, wherein the pro-angiogenic protein is vascular endothelial growth factor (VEGF).

43. The method of embodiment 42, wherein the transcription factor is a non-naturally-occurring zinc finger protein that activates transcription of the VEGF gene.

44. The method of any of embodiments 8, 9, or 13, further comprising administering a pro-angiogenic agent along with the SB623 cells.

45. The method of embodiment 44, wherein the endothelial cells are in a subject.

46. The method of embodiment 45, wherein the endothelial cells are in the central nervous system of the subject.

47. The method of embodiment 46, wherein the endothelial cells are in the brain of the subject.

48. The method of embodiment 44, wherein the pro-angiogenic agent is a nucleic acid.

49. The method of embodiment 44, wherein the pro-angiogenic agent is a polypeptide.

50. The method of embodiment 49, wherein the polypeptide is a transcription factor that activates expression of a pro-angiogenic protein.

51. The method of embodiment 50, wherein the pro-angiogenic protein is vascular endothelial growth factor (VEGF).

52. The method of embodiment 51, wherein the transcription factor is a non-naturally-occurring zinc finger protein that activates transcription of the VEGF gene.

53. The method of embodiment 17, further comprising administering a pro-angiogenic agent along with the SB623 cells.

54. The method of embodiment 53, wherein the blood vessels are in a subject.

55. The method of embodiment 54, wherein the blood vessels are in the central nervous system of the subject.

56. The method of embodiment 55, wherein the blood vessels are in the brain of the subject.

57. The method of embodiment 53, wherein the pro-angiogenic agent is a nucleic acid.

58. The methot f embodiment 53, wherein the pro-angiogenic agent s a polypeptide.

59. The method of embodiment 58, wherein the polypeptide is a transcription factor that activates expression of a pro-angiogenic protein.

60. The method of embodiment 59, wherein the pro-angiogenic protein is vascular endothelial growth factor (VEGF).

61. The method of embodiment 60, wherein the transcription factor is a non-naturally-occurring zinc finger protein that activates transcription of the VEGF gene.

62. A method for providing an angiogenic factor to a subject, wherein the method comprises administering to the subject a population of SB623 cells; wherein the SB623 cells are obtained by (a) providing a culture of mesenchymal stem cells, (b) contacting the cell culture of step (a) with a polynucleotide comprising sequences encoding a Notch intracellular domain (NICD) wherein said polynucleotide does not encode a full-length Notch protein, (c) selecting cells that comprise the polynucleotide of step (b), and (d) further culturing the selected cells of step (c) in the absence of selection.

63. The method of embodiment 62, wherein the subject is suffering from an ischemic disorder.

64. The method of embodiment 63, wherein the subject is suffering from a disease or disorder of the central nervous system.

65. The method of embodiment 62, wherein the trophic factor is selected from the group consisting of one or more of angiogenin, angiopoietin-2, epidermal growth factor, basic fibroblast growth factor, heparin-binding epithelial growth factor-like growth factor, hepatocyte growth factor, leptin, platelet-derived growth factor-BB, placental growth factor and vascular endothelial growth factor.

66. The method of embodiment 65, wherein the trophic factor is vascular endothelial growth factor.

67. A method for providing vascular endothelial growth factor to a subject, wherein the method comprises administering to the subject a population of SB623 cells; wherein the SB623 cells are obtained by (a) providing a culture of mesenchymal stem cells, (b) contacting the cell culture of step (a) with a polynucleotide comprising sequences encoding a Notch intracellular domain (NICD) wherein said polynucleotide does not encode a full-length Notch protein, (c) selecting cells that comprise the polynucleotide of step (b), and (d) further culturing the selected cells of step (c) in the absence of selection.

68. The method of embodiment 67, wherein the subject is suffering from an ischemic disorder.

69. The method of embodiment 68, wherein the subject is suffering from a disease or disorder of the central nervous system.

BRIEF DESCRIPTION OF THE DRAWINGS

FIG. 7A shows counts of new vessels and of branchpoints in the new vessels. For each of the three pairs of bars, the left bar shows measurements of new vessel formation and the right bar shows measurements of vessel branching. The left-most pair of bars ("Control") shows results obtained from control aortic rings; the center pair of bars ("MSC CM") shows results obtained from aortic rings cultured for 10 days in MSC conditioned medium; and the right-most pair of bars ("SB623 CM") shows results obtained from aoritc rings cultured for 10 days in SB623 cell conditioned medium.

FIG. 7B show ratios of branchpoints to new vessels for control aortic rings (left bar), rings cultured 10 days in MSC conditioned medium (center bar) and rings cultured 10 days in SB623 cell conditioned medium (right bar).

Values shown are Mean±SEM for 7 donor pairs. "*" indicates $p<0.05$ compared to control group.

Figure 8:
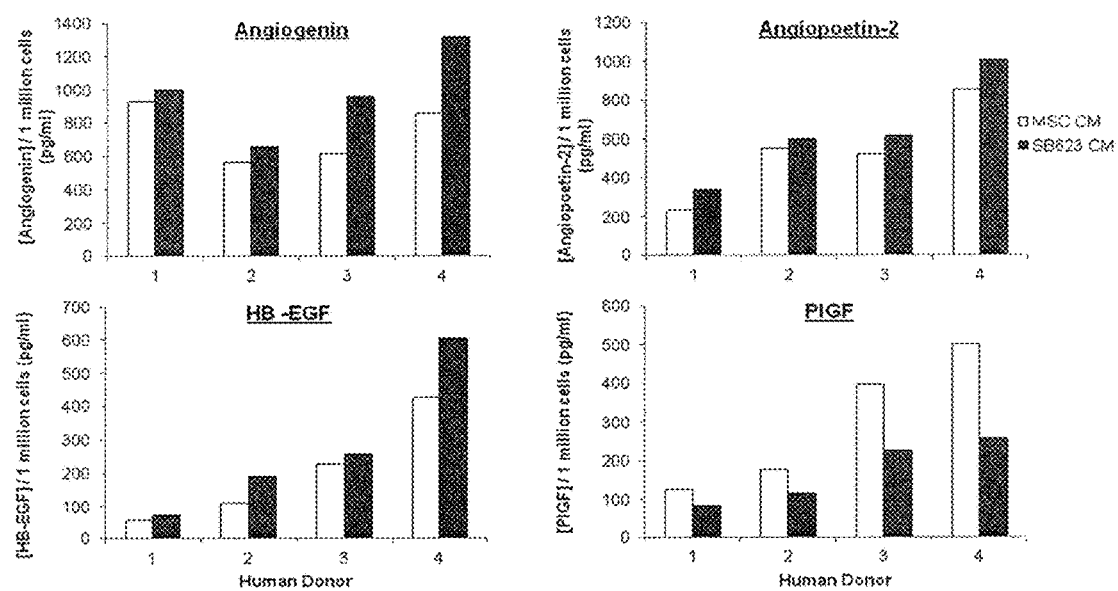

FIG. 8 shows levels of four different trophic factors in conditioned medium from MSCs (light bars) and SB623 cells (dark bars). Protein levels are expressed as picograms per ml of conditioned medium per $10^6$ cells. Conditioned media from MSCs (and SB623 cells derived therefrom) from four different human donors were tested, as indicated in the figure. Levels of angiogenin, angiopoietin-2, heparin-binding epidermal growth factor-like growth factor (HB-EGF), and placental growth factor (PlGF) are shown.

Figure 9:
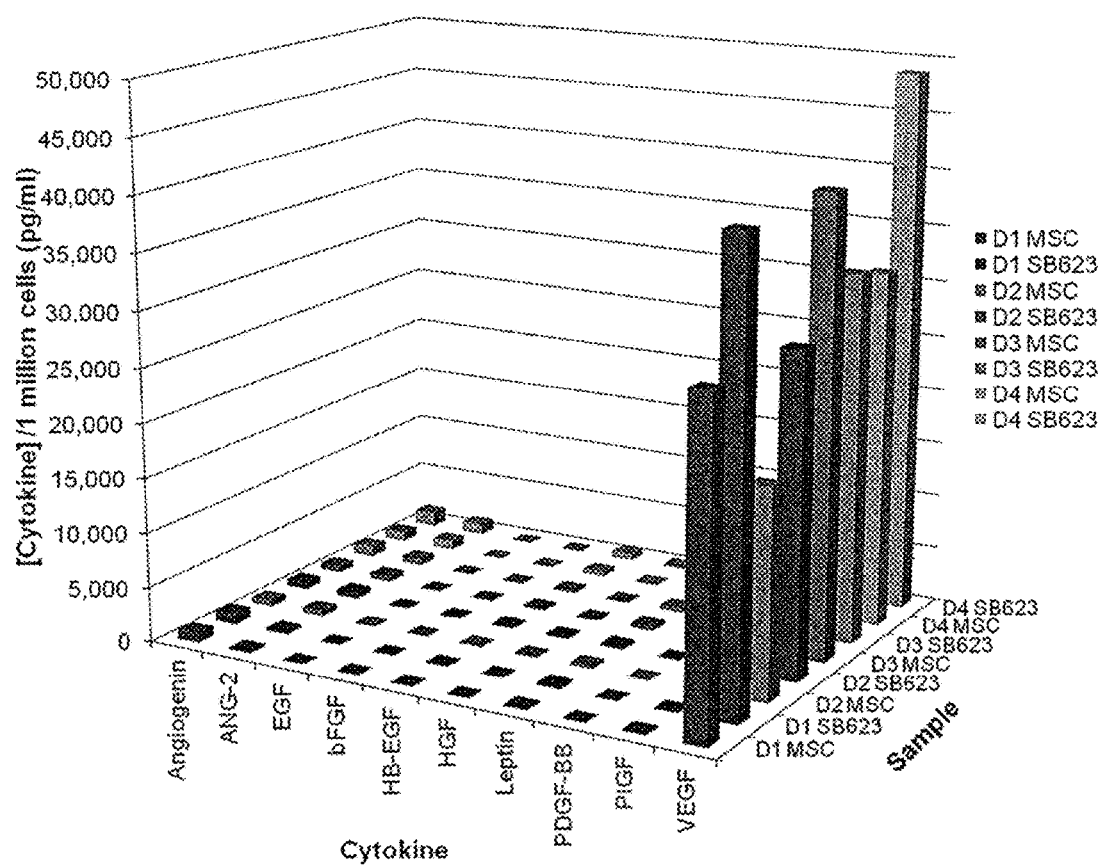

FIG. 9 shows levels of ten different cytokines in conditioned medium from MSCs and SB623 cells. Cells for production of conditioned medium were obtained from four different donors (D1, D2, D3 and D4), as indicated in the figure. This figure highlights the vast amounts of VEGF produced by MSCs and SB623 cells, compared to the levels of the other trophic factors tested. Abbreviations are given in the legend to Table 1 (Example 6).

Figure 10A:
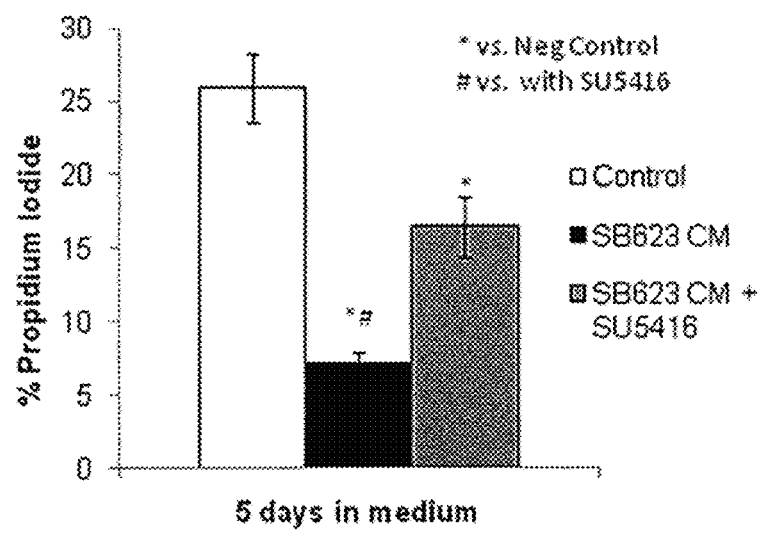
Figure 10B:
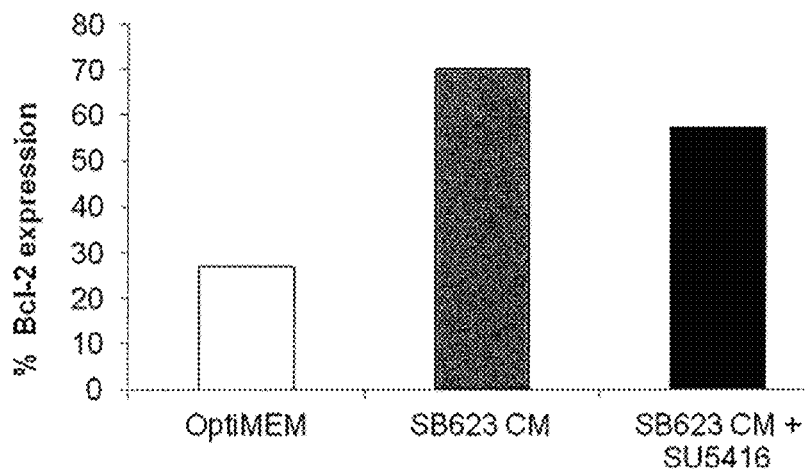

FIGS. 10A and 10B show the effects of a VEGF receptor inhibitor on improvements in HLTVEC viability promoted by SB623 cell-conditioned medium. FIG. 10A shows the fraction of cells permeable to propidium iodide in cultures of HUVECs that had been starved for serum and growth factors. Left-most bar shows results obtained from control serum/growth factor-starved HUVECs; center bar shows results for serum/growth factor-starved HUVECs cultured for five days in the presence of conditioned medium from SB623 cells, and the right-most bar shows results for ser-tunlgrowth factor-starved HUVECs cultured for five days in the presence of conditioned medium from SB623 cells and 50 nM SU5416. Results were averaged from two donors; "*" indicates $p<0.05$ with respect to control cultures; "#" indicates $p<0.05$ with respect to cultures exposed to SB623 cell conditioned medium and SU5416.

FIG. 10B shows measurement of the fraction of cells expressing Bcl-2 in a culture of HUVECs that had been starved for serum and growth factors. Left-most bar shows results obtained from control serum/growth factor-starved HUVECs; center bar shows results for serum/growth factor-starved HUVECs cultured for five days in the presence of conditioned medium from SB623 cells, and the right-most bar shows results for serum/growth factor-starved HUVECs cultured for five days in the presence of conditioned medium from SB623 cells and 50 nM SU5416. Results, averaged from duplicate donors, were obtained by measuring fluorescence of cells stained with a fluorescein-conjugated anti-Bcl-2 antibody and subtracting fluorescence of cells exposed to fluorescein-conjugated IgG.

Figure 11:
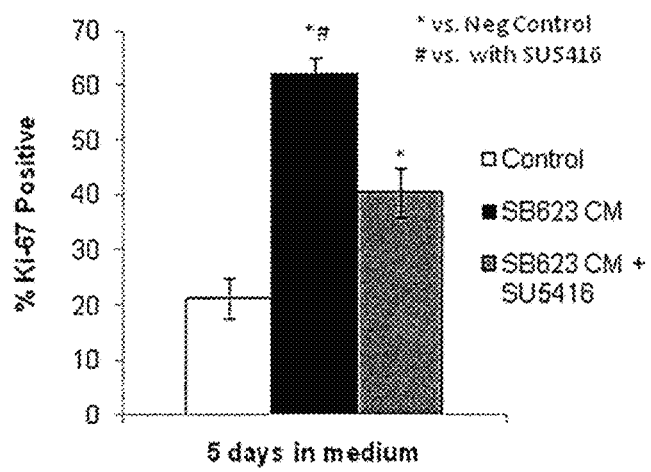

FIG. 11 shows measurement of the fraction of cells expressing Ki67 in HUVEC cultures exposed to SB623 cell conditioned medium in the presence and absence of the VEGFR2 inhibitor SU5416, and by control cells cultured in the absence of CM. The left-most (clear) bar shows results obtained from control serum/growth factor-starved HUVECs; the center (black) bar shows results for serum/growth factor-starved HUS ECs cultured in the presence of conditioned medium from SB623 cells, and the right-most (gray) bar shows results for serumlgrowth factor-starved HUVECs cultured in the presence of conditioned medium from SB623 cells and 50 nM SU5416. Values shown are mean+SEM for two separate donors of SB623 cells. "*" indicates $p<0.05$ with respect to the negative control cultures (no conditioned medium); "#" indicates $p<0.05$ with respect to SU5416-treated cultures.

Figure 12:
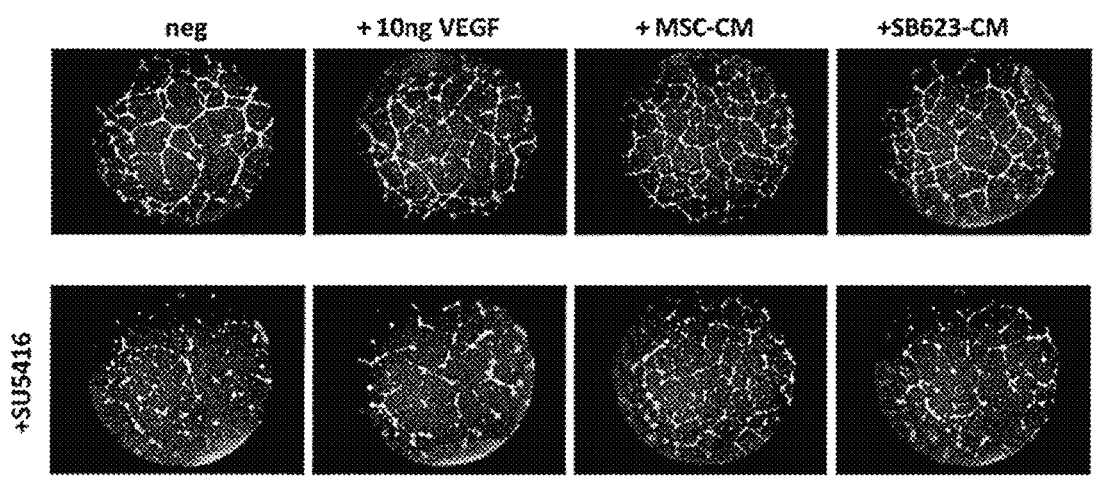

FIG. 12 shows the effects of a VEGF receptor inhibitor on the enhancement of tube formation by HUVECs promoted by MSC- and SB623 cell-conditioned media. The top row shows cells cultured in the absence of the inhibitor. The left-most panel of the top row ("neg") shows a phase-contrast photomicrograph of control HUVECs following culture for 16 hours in Opti-MEM Medium. The second panel from the left ("+10 ng VEGF") shows a phase-contrast photomicrograph of HUVECs following culture for 16 hours in Opti-MEM Medium to which 10 ng/ml VEGF was added. The third panel from the left. ("+MSC-CM") shows a phase-contrast photomicrograph of HUVECs following culture for 16 hours in MSC-conditioned medium. The right-most panel ("+SB623-CM") shows a phase-contrast photomicrograph of HUVECs following culture for 16 hours in SB623 cell-conditioned medium. Panels in the bottom row show photomicrographs of HUVECs under the same conditions as in the top row but with the addition of 50 nM SU5416.

Figure 13:
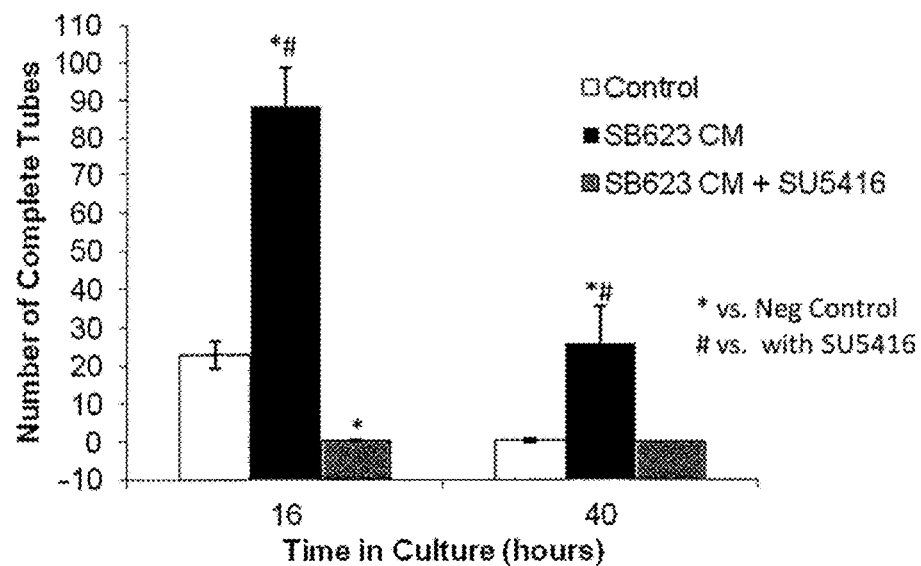

FIG. 13 shows quantitation of tube formation by HUVECs exposed to SB623 cell conditioned medium in the presence and absence of the VEGFR2 inhibitor SU5416, and by control cells cultured in the absence of CM.

For each time point, the left-most (clear) bar shows results obtained from control serum/growth factor-starved HUVECs; the center (black) bar shows results for serum/growth factor-starved HUVECs cultured in the presence of conditioned medium from SB623 cells, and the right-most (gray) bar shows results for serum/growth factor-starved HUVECs cultured in the presence of conditioned medium from SB623 cells and 50 nM SU5416. Values shown are mean+SEM for three separate donors of SB623 cells. "*" indicates $p<0.05$ with respect to the negative control cultures (no conditioned medium); "#" indicates $p<0.05$ with respect to SU5416-treated cultures.

Figure 14:
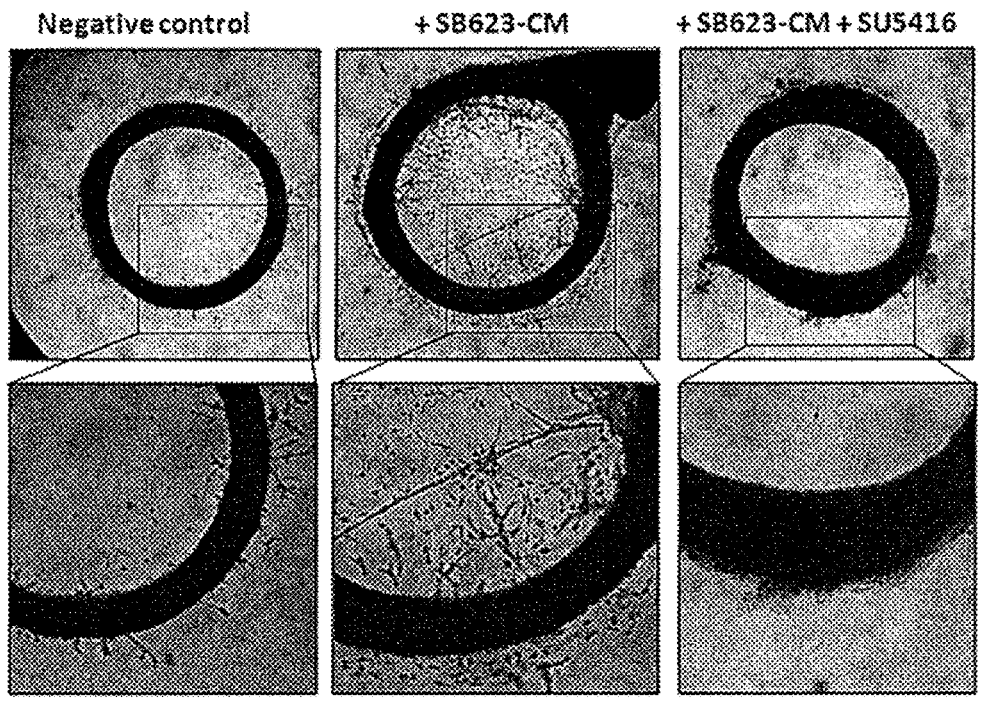

FIG. 14 shows the effects of a VEGF receptor inhibitor on enhancement of vessel outgrowth and branching promoted by SB623 cell-conditioned medium in an aortic ring assay. In the upper row, the left panel shows a photomicrograph of an aortic ring after culture for 10 days on a RGF-basement gel in OptiMEM medium ("Negative control"). The center panel shows a photomicrograph of an aortic ring after culture for 10 days in SB623 cell conditioned medium ("SB623-CM"). The right panel shows a photomicrograph of an aortic ring after culture for 10 days in SB623 cell conditioned medium containing 50 nM SU5416 ("+SB623-CM+SU5416"). Enlargements of certain regions of each photomicrograph are shown in the lower row.

DETAILED DESCRIPTION

Disclosed herein are new methods and compositions for modulation of angiogenesis. In particular, factors secreted by SB623 cells (cells descended from MSCs that have been transfected with a vector containing sequences encoding a Notch intracellular domain) promote survival and proliferation of endothelial cells in vitro under serum- and growth factor-deprived conditions, and stimulate vascular tube formation by human umbilical vein endothelial cells. In addition, conditioned medium from SB623 cells promoted endothelial sprouting and branching in a rodent aortic ring assay.

Practice of the present disclosure employs, unless otherwise indicated, standard methods and conventional techniques in the fields of cell biology, toxicology, molecular biology, biochemistry, cell culture, immunology, oncology, recombinant DNA and related fields as are within the skill of the art. Such techniques are described in the literature and thereby available to those of skill in the art. See, for example, Alberts, B. et al., "Molecular Biology of the Cell," 5$^{th}$ edition, Garland Science, New York, N.Y., 2008; Voet, D. et al. "Fundamentals of Biochemistry: Life at the Molecular Level," 3$^{rd}$ edition, John Wiley & Sons, Hoboken, N.J., 2008; Sambrook, J. et al., "Molecular Cloning: A Laboratory Manual," 3$^{rd}$ edition, Cold Spring Harbor Laboratory Press, 2001; Ausubel, F. et al., "Current Protocols in Molecular Biology," John Wiley & Sons New York, 1987 and periodic updates; Freshney, R. I., "Culture of Animal Cells: A Manual of Basic Technique," 4$^{th}$ edition, John Wiley & Sons, Somerset, N.J., 2000; and the series "Methods in Enzymology," Academic Press, San Diego, Calif.

For the purposes of the present. disclosure, "angiogenesis" refers to the formation of new vasculature (e.g., blood vessels; e.g., veins, arteries, venules arterioles, capillaries). Angiogenesis can occur by sprouting of new vessels from an existing vessel, and/or by branching of a vessel. Angiogenesis also includes the attendant processes of matrix remodeling and cell recruitment (e.g., recruitment of smooth muscle cells, monocytes and/or pericytes).

"MSCs" refer to adherent, non-hematopoietic stem cells obtained from bone marrow. These cells are variously known as mesenchymal stem cells, mesenchymal stromal cells, marrow adherent stromal cells, marrow adherent stem cells and bone marrow stromal cells.

Stroke

"Stroke" is the name given to conditions resulting from impairment of blood flow in the brain. Such cerebrovascular impairment can result, for example, from intracranial hemorrhage, or from reduction or blockage of blood flow in the brain (i.e., cerebral ischemia). Ischemic blockages can result from thrombosis (i.e., formation of a clot in situ in a cranial vessel or a vessel supplying the brain) or from a cerebral embolism migration of a clot to a site in the brain). The damage resulting from ischemic or hemorrhagic stroke usually results in impairment of neurological function. Additional information relating to different types of stroke, and their characteristics, is found in co-owned U.S. Pat. No. 8,092,792; the disclosure of which is incorporated by reference in its entirety herein for the purpose of describing different types of stroke and their characteristics.

Mesenchymal Stem Cells (MSCs)

The present disclosure provides methods for promoting angiogenesis by transplanting SB623 cells to a site of ischemic injury in a subject. SB623 cells are obtained from marrow adherent stromal cells, also known as mesenchymal stem cells (MSCs), by expressing the intracellular domain of the Notch protein in the MSCs. MSCs are obtained by selecting adherent cells (i.e., cells that adhere to tissue culture plastic) from bone marrow.

Exemplary disclosures of MSCs are provided in U.S. patent application publication No. 2003/0003090; Prockop (1997) Science 276:71-74 and Jiang (2002) Nature 418:41-49. Methods for the isolation and purification of MSCs can be found, for example, in U.S. Pat. No. 5,486,359; Pittenger et al. (1999) Science 284:143-147 and Dezawa et al. (2001) Eur. J. Neurosci. 14:1771-1776. Human MSCs are commercially available (e.g., BioWhittaker, Walkersville, Md.) or can be obtained from donors by, e.g., bone marrow aspiration, followed by selection for adherent bone marrow cells. See, e.g., WO 2005/100552.

MSCs can also be isolated from umbilical cord blood. See, for example, Campagnoli et al. (2001) Blood 98:2396-2402; Erices et al. (2000) Br. J. Haematol. 109:235-242 and Hou et al. (2003) Int. Hematol. 78:256-261.

Notch Intracellular Domain

The Notch protein is a transmembrane receptor, found in all metazoans, that influences cell differentiation through intracellular signaling. Contact of the Notch extracellular domain with a Notch ligand (e.g., Delta, Serrate, Jagged) results in two proteolytic cleavages of the Notch protein, the second of which is catalyzed by a γ-secretase and releases the Notch intracellular domain (NICD) into the cytoplasm. In the mouse Notch protein, this cleavage occurs between amino acids gly1743 and val1744. The NICD translocates to the nucleus, where it acts as a transcription factor, recruiting additional transcriptional regulatory proteins (e.g., MAM, histone acetylases) to relieve transcriptional repression of various target genes (e.g., Hes 1).

Additional details and information regarding Notch signaling are found, for example in Artavanis-Tsakonas et al. (1995) Science 268:225-232; Mumm and Kopan (2000) Develop. Biol. 228:151-165 and Ehebauer et al. (2006) Sci. STKE 2006 (364), cm7. [DOI: 10.1126/stke.3642006cm7].

Cell Culture and Transfection

Standard methods for cell culture are known in the art. See, for example, R. I. Freshney "Culture of Animal Cells: A Manual of Basic Technique," Fifth Edition, Wiley, New York, 2005.

Methods for introduction of exogenous DNA into cells (i.e., transfection) are also well-known in the art. See, for example, Sambrook et al "Molecular Cloning: A Laboratory Manual," Third Edition, Cold Spring Harbor Laboratory Press, 2001; Ausubel et al., "Current Protocols in Molecular Biology," John Wiley & Sons, New York, 1987 and periodic updates.

SB623 Cells

In one embodiment for the preparation of SB623 cells, a culture of MSCs is contacted with a polynucleotide comprising sequences encoding a Notch intracellular domain (MCD): e.g., by transfection; followed by enrichment of transfected cells by drug selection and further culture. See, for example, U.S. Pat. No. 7,682,825 (Mar. 23, 2010); U.S. Patent Application Publication No. 2010/0266554 (Oct. 21, 2010); and WO 2009/023251 (Feb. 19, 2009); all of whiCh disclosures are incorporated by reference, in their entireties, for the purposes of describing isolation of mesenchymal stem cells and conversion of mesenchymal stem cells to SB623 cells (denoted "neural precursor cells" and "neural regenerating cells" in those documents).

In these methods, any polynucleotide encoding a Notch intracellular domain e.g., vector) can be used, and any method for the selection and enrichment of transfected cells can be used. For example, in certain embodiments, MSCs are transfected with a vector containing sequences encoding a Notch intracellular domain and also containing sequences encoding a drug resistance marker (e.g. resistance to G418). In additional embodiments, two vectors, one containing sequences encoding a Notch intracellular domain and the other containing sequences encoding a drug resistance marker, are used for transfection of MSCs. In these embodiments, selection is achieved, after transfection of a cell culture with the vector or vectors, by adding a selective agent (e.g., G418) to the cell culture in an amount sufficient to kill cells that do not comprise the vector but spare cells that do. Absence of selection entails removal of said selective agent or reduction of its concentration to a level that does not kill cells that do not comprise the vector. Following selection e.g., for seven days) the selective agent is removed and the cells are further cultured (e.g., for two passages).

Preparation of SB623 cells thus involves transient expression of an exogenous Notch intracellular domain in a MSC. To this end, MSCs can be transfected with a vector comprising sequences encoding a Notch intracellular domain wherein said sequences do not encode a full-length Notch protein. All such sequences are well known and readily available to those of skill in the art. For example, Del Amo et al. (1993) *Genomics* 15:259-264 present the complete amino acid sequences of the mouse Notch protein; while Mumm and Kopan (2000) *Devel. Biol.* 228:151-165 provide the amino acid sequence, from mouse Notch protein, surrounding the so-called S3 cleavage site which releases the intracellular domain. Taken together, these references provide the skilled artisan with each and every peptide containing a Notch intracellular domain that is not the full-length Notch protein; thereby also providing the skilled artisan with every polynucleotide comprising sequences encoding a Notch intracellular domain that does not encode a full-length Notch protein. The foregoing documents (Del Amo and Mumm) are incorporated by reference in their entireties for the purpose of disclosing the amino acid sequence of the full-length Notch protein and the amino acid sequence of the Notch intracellular domain, respectively.

Similar information is available for Notch proteins and nucleic acids from additional species, including rat, *Xenopus, Drosophila* and human. See, for example. Weinmaster et al. (1991) *Development* 113:199-205; Schroeter et al. (1998) *Nature* 393:382-386; NCBI Reference Sequence No. NM_017167 (and references cited therein); SwissProt P46531 (and references cited therein): SwissProt. Q01705 (and references cited therein); and GenBank CAB40733 (and references cited therein). The foregoing references are incorporated by reference in their entireties for the purpose of disclosing the amino acid sequence of the full-length Notch protein and the amino acid sequence of the Notch intracellular domain in a number of different species.

In additional embodiments, SB623 cells are prepared by introducing, into MSCs, a nucleic acid comprising sequences encoding a Notch intracellular domain such that the MSCs do not express exogenous Notch extracellular domain. Such can be accomplished, for example, by transfecting MSCs with a vector comprising sequences encoding a Notch intracellular domain wherein said sequences do not encode a full-length Notch protein.

Additional details on the preparation of SB623 cells, and methods for making cells with properties similar to those of SB623 cells which can be used in the methods disclosed herein, are found in U.S. Pat. No. 7,682,825; and U.S. Patent Application Publication Nos. 2010/0266554 (Oct. 21, 2010) and 2011/0229442 (Sep. 22, 2011); the disclosures of which are incorporated by reference herein for the purposes of providing additional details on, and alternative methods for the preparation of, SB623 cells, and for providing methods for making cells with properties similar to those of SB623 cells. See also Dezawa et al. (2004) *J. Clin. Invest.* 113:1701-1710.

Uses

As disclosed herein, the inventors have discovered that descendants of mesenchymal stem cells in which a Notch intracellular domain has been transiently expressed (i.e., SB623 cells) have angiogenic activity; and that said cells synthesize and secrete angiogenic factors. Accordingly, transplantation of SB623 cells is useful for treatment of disorders in which a therapeutic benefit can be achieved by increasing angiogenesis in a subject. Such disorders include, but are not limited to, cerebral ischemia (e.g., stroke), cardiac ischemia ischemic heart disease), ischemia of the bowel ischemic colitis, mesenteric ischemia), ischemia of the limb, cutaneous ischemia, ocular ischemic syndrome (e.g., retinal ischemia) and cerebral palsy.

Thus, SB623 cells as described herein can be used in a number of methods related to stimulation of angiogenesis. These include, but are not limited to, treatment of any of the disorders mentioned in the previous paragraph, augmentation of angiogenesis, repair of ischemic damage, preventing death of endothelial cells, enhancing survival of endothelial cells, stimulating proliferation of endothelial cells, and/or enhancing the branching of blood vessels.

Such methods can be performed in vitro or in a subject. The subject can be a mammal, preferably a human. Stimulation of angiogenesis by SB623 cells, and the attendant effects of such stimulation as disclosed herein, can occur, for example, in the central nervous system (e.g., in the brain).

Transplantation of SB623 cells can also be used in methods for providing one or more angiogenic trophic factors to a subject. Such factors include, but are not limited to, angiogenin, angiopoietin-2, epidermal growth factor, basic fibroblast growth factor, heparin-binding epithelial growth factor-like growth factor, hepatocyte growth factor, leptin platelet-derived growth factor-BB, placental growth factor and vascular endothelial growth factor.

In additional embodiments, SB623 cells can be used in combination with a second pro-angiogenic agent, in combination therapies for increasing angiogenesis in a subject. Said combination therapies can be used for all of the purposes set forth above. The second pro-angiogenic agent can be, e.g., a small molecule drug, a nucleic acid or a polypeptide (e.g., antibody, transcription factor). Exemplary nucleic acids are triplex-forming nucleic acids, ribozymes and siRNAs that activate expression of angiogenic proteins andlor block expression of anti-angiogenic proteins. Exemplary antibodies are those that bind to andlor inhibit the activity of angiogenic proteins (or other angiogenic agents). Exemplary transcription factors are those that inhibit transcription of a gene encoding one or more anti-angiogenic protein(s), as well as those that activate the transcription of one or more pro-angiogenic protein(s). Anti-angiogenic and pro-angiogenic proteins are known in the art. Exemplary anti-angiogenic proteins include pigment epithelium derived factor (PERF) and placental growth factor (PlGF). Exemplary pro-angiogenic proteins include vascular endothelial growth factor (VEGF) angiopoietin, and hepatocyte growth factor (HGF).

In certain embodiments, transcription factors as disclosed above are non-naturally-occurring engineered) transcription factors. An example of such a non-naturally-occurring transcription factor is a non-naturally-occurring zinc finger protein that has been engineered to bind to a DNA sequence in cellular chromatin that regulates transcription of a target gene (e.g., a VEGF gene). Said engineered zinc finger transcription factors comprise, in addition to an engineered zinc finger DNA-binding domain, a transcriptional regulatory domain (e.g., a transcriptional activation domain or a transcriptional repression domain), as are known in the art.

Methods for engineering zinc finger DNA binding domains, to bind to a DNA sequence of choice, are well-known in the art. See, for example, Beerli et al. (2002) *Nature Biotechnol.* 20:135-141; Pala et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. Zinc finger binding domain are engineered to have a novel binding specificity, compared to a naturally-occurring zinc finger protein. Engineering methods include, but are not limited to, rational design and various types of empirical selection methods. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Patent Application. Publication Nos. 2002/0165356; 2004/0197892; 2007/0154989; 2007/0213269; and International Patent Application Publication Nos. WO 98/53059 and WO 2003/016496.

Exemplary selection methods, including phage display, interaction trap, hybrid selection and two-hybrid systems, are disclosed in U.S. Pat. Nos. 5,789,538; 5,925,523; 6,007,988; 6,013,453; 6,140,466; 6,200,759; 6,242,568; 6,410,248; 6,733,970; 6,790,941; 7,029,847 and 7,297,491; as well as U.S. Patent Application Publication Nos. 2007/0009948 and 2007/0009962; WO 98/37186; WO 01/60970 and GB 2,338,237.

Enhancement of binding specificity for zinc forger binding domains has been described, for example, in U.S. Pat. No. 6,794,136 (Sep. 21, 2004). Additional aspects of zinc finger engineering, with respect to inter-finger linker sequences, are disclosed in U.S. Pat. No. 6,479,626 and U.S. Patent Application Publication No. 2003/0119023. See also Moore et al. (2001a) *Proc. Natl. Acad. Sci. USA* 98:1432-1436; Moore et al. (200b) *Proc. Natl. Acad. Sci. USA* 98:1437-1441 and WO 01/53480.

Transcriptional activation and repression domain are known in the art. See, e.g., Science 269:630 (1995). Exemplary transcriptional activation domains include p65, VP16 and VP64. Exemplary transcriptional repression domains include KRAB, KAP-1, MAD, FKHR, ERD and SID. Functional domains from nuclear hormone receptors can act as either activators or repressors, depending upon the presence of a ligand. See also U.S. Pat. No. 7,985,887.

Formulations, Kits and Routes of Administration

Therapeutic compositions comprising SB623 cells as disclosed herein are also provided. Such compositions typically comprise the SB623 cells and a pharmaceutically acceptable carrier. Supplementary active compounds can also be incorporated into SB623 cell compositions (see below).

The therapeutic compositions disclosed herein are useful for, inter alia, stimulating angiogenesis after occurrence of a stroke or other ischemic injury in a subject. Accordingly, a "therapeutically effective amount" of a composition comprising SB623 cells can be any amount that stimulates angiogenesis. For example, dosage amounts can vary from about 100; 500; 1,000; 2,500; 5,000; 10,000; 20,000; 50,000; 100,000; 500,000; 1,000,000; 5,000,000 to 10,000,000 cells or more (or any integral value therebetween); with a frequency of administration of, e.g., once per day, twice per week, once per week, twice per month, once per month, depending upon, e.g., body weight, route of administration, severity of disease, etc.

Various pharmaceutical compositions and techniques for their preparation and use are known to those of skill in the art in light of the present disclosure. For a detailed listing of suitable pharmacological compositions and techniques for their administration one may refer to texts such as Remington's Pharmaceutical Sciences, 17th ed. 1985; Brunton et al., "Goodman and Gilman's The Pharmacological Basis of Therapeutics," McGraw-Hill, 2005 University of the Sciences in. Philadelphia (eds.) "Remington: The Science and Practice of Pharmacy," Lippincott Williams & Wilkins, 2005: and University of the Sciences in Philadelphia (eds.), "Remington: The Principles of Pharmacy Practice," Lippincott Williams & Wilkins, 2008.

The cells described herein can be suspended in a physiologically compatible carrier for transplantation. As used herein, the term "physiologically compatible carrier" refers to a carrier that is compatible with the SB623 cells and with any other ingredients of the formulation, and is not deleterious to the recipient thereof. Those of skill in the art are familiar with physiologically compatible carriers. Examples of suitable carriers include cell culture medium (e.g., Eagle's minimal essential medium), phosphate buffered saline, Hank's balanced salt solution+/−glucose (HBSS), and multiple electrolyte solutions such as Plasma-Lyte™ A (Baxter).

The volume of a SB623 cell suspension administered to a patient will vary depending on the site of implantation, treatment goal and number of cells in solution. Typically the amount of cells administered to a patient will be a therapeutically effective amount. As used herein, a "therapeutically effective amount" or "effective amount" refers to the number of transplanted cells which are required to effect treatment of the particular disorder; i.e., to produce a reduction in the amount and/or severity of the symptoms associated with that disorder. For example, in the case of stroke, transplantation of a therapeutically effective amount of SB623 cells results in new vessel growth, vessel sprouting and vessel branching, e.g., in an area that has been damaged by ischemic. Therapeutically effective amounts vary with the type and extent of ischemic damage, and can also vary depending on the overall condition of the subject.

The disclosed therapeutic compositions can also include pharmaceutically acceptable materials, compositions or vehicles, such as a liquid or solid filler, diluent, excipient, solvent or encapsulating material, i.e., carriers. These carriers can, for example, stabilize the SB623 cells and/or facilitate the survival of the SP623 cells in the body. Each carrier should be "acceptable" in the sense of being compatible with the other, ingredients of the formulation and not injurious to the subject. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Exemplary formulations include, but are not limited to, those suitable for parenteral administration, e.g., intrapuhnonary, intravenous, intra-arterial, intra-ocular, intra-cranial, sub-meningial, or subcutaneous administration, including formulations encapsulated in micelles, liposomes or drug-release capsules (active agents incorporated within a biocompatible coating designed for slow-release); ingestible formulations; formulations for topical use, such as eye drops, creams, ointments and gels; and other formulations such as inhalants, aerosols and sprays. The dosage of the compositions of the disclosure will vary according to the extent and severity of the need for treatment, the activity of the administered composition, the general health of the subject, and other considerations well known to the skilled artisan.

In additional embodiments, the compositions described herein are delivered locally to a site of ischemic damage. Localized delivery allows for the delivery of the composition non-systemically, thereby reducing the body burden of the composition as compared to systemic delivery. Such local delivery can be achieved, for example, by intra-cranial injection, or through the use of various medically implanted devices including, but not limited to, stems and catheters, or can be achieved by inhalation, phlebotomy, or surgery. Methods for coating, implanting, embedding, and otherwise attaching desired agents to medical devices such as stents and catheters are established in the art and contemplated herein.

Another aspect of the present disclosure relates to kits for carrying out the administration of SB623 cells, optionally in combination with another therapeutic agent, to a subject. In one embodiment, a kit comprises a composition of SB623 cells, formulated in a pharmaceutical carrier, optionally containing, e.g., a pro-angiogenic agent (see below), formulated as appropriate, in one or more separate pharmaceutical preparations.

Combination Therapies

In certain embodiments, SB623 cell compositions can be used in combination with other compositions comprising substances that stimulate angiogenesis ("pro-angiogenic agents"), e.g., for treatment of stroke. The compositions can be administered sequentially in any order or concurrently. Accordingly, therapeutic compositions as disclosed herein can contain both SB623 cells and a pro-angiogenic agent. In additional embodiments, separate therapeutic compositions, one comprising SB623 cells and the other comprising a pro-angiogenic agent, can be administered to the subject, either separately or together.

In certain embodiments, a pro-angiogenic agent is a protein (e.g., fibroblast growth factor, platelet-derived growth factor, transforming growth factor alpha, hepatocyte growth factor, vascular endothelial growth factor, sonic hedgehog, MAGP-2, HIF-1, PR-39, RTEF-1, c-Myc, TFII, Egr-1, ETS-1) or a nucleic acid encoding such a protein. See, for example, Vincent et al. (2007) *Gene Therapy* 14:781-789. In other embodiments, a pro-angiogenic agent can be a small. RNA molecule (e.g., siRNA, shRNA, microRNA) or a ribozyme that targets a nucleic acid encoding an inhibitor of angiogenesis. In additional embodiments, a pro-angiogenic agent can be a triplex-forming nucleic acid that binds to DNA sequences regulating the expression of a protein that inhibits angiogenesis, such as to block transcription of the gene encoding the protein.

In additional embodiments, a pro-angiogenic agent is a transcription factor that activates expression of a pro-angiogenic molecule (e.g., protein). Naturally-occurring transcription factors (such as, for example, HIF-1alpha) that regulate the expression of pro-angiogenic proteins, are known. In addition, synthetic transcriptional regulatory proteins can be constructed by genetic engineering. For example, methods for the design of zinc finger DNA-binding domains that bind to a sequence of interest, and methods for the fusion of such zinc finger DNA-binding domains to transcriptional activation and repression domains, have been described. See, for example, U.S. Pat. Nos. 6,534,261: 6,607,882; 6,785,613; 6,794,136; 6,824,978; 6,933,1 6,979,539; 7,013,219: 7,177,766; 7,220,719; and 7,788,044. These methods can be used to synthesize non-naturally-occurring proteins that activate transcription of any gene encoding a pro-angiogenic protein. hi addition, synthetic zinc finger transcriptional activators of the vascular endothelial growth factor (VEGF) gene have been described. See, e.g., U.S. Pat. Nos. 7,026,462; 7,067,317; 7,560,440: 7,605,140; and 8,071,564. Accordingly, a non-naturally-occurring (i.e., synthetic) zinc finger protein that activates transcription of the VEGF gene can be used, in combination with SB623 cells, for augmenting angiogenesis, e.g., in the treatment of stroke.

In additional embodiments, a natural or synthetic transcriptional regulatory protein (e.g., a synthetic zinc finger transcriptional regulatory protein) that inhibits transcription of an anti-angiogenic molecule can be used as a pro-angiogenic agent.

EXAMPLES

Example 1

Conditioned Medium

MSCs and SB623 cells were obtained and/or prepared as described. See, for example, U.S. Pat. No. 7,682,825 (Mar. 23, 2010) and U.S. Patent Application Publications Nos. 2010/0266554 (Oct. 21, 2010), 201010310529 (Dec. 9, 2010), 2011./02.29442 (Sep. 22., 2011), and 201110306137 (Dec. 15, 2011); the disclosures of which are incorporated by reference in their entireties for the purposes of describing the preparation of SB623 cells (variously referred to as "neural precursor cells" and "neural regenerating cells" in those documents). Cells were cultured in growth medium, which contained alpha-MEM (Mediatech, Herndon, Va.) supplemented with 10% fetal bovine serum (FBS, Hyclone, Logan, Utah), 2 mM L-glutamine and 1% penicillin/streptomycin (both from Invitrogen, Carlsbad, Calif.). MSCs and SB623 cells typically expressed CD29, CD90 and CD105; and did not express CD31, CD34, or CD45, as determined by flow cytometry.

For use in the experiments described herein, frozen MSCs and SB623 cells from the same human donor were thawed, re-plated in growth medium, and allowed to recover for approximately one week. To obtain conditioned medium, cells were grown to approximately 90% confluence (~45,000 cells:cm), the plates were rinsed once with phosphate buffered saline (PBS) and the medium was then replaced with OptiMEM® medium (Invitrogen, Carlsbad, Calif.), maintaining the same cell density. Conditioned medium was collected 72 hours later. Frozen samples of conditioned medium were slowly warmed to 37° C. prior to use.

Example 2

Effect of SB623 Cell-secreted Factors on HUVEC Survival

Cerebral ischemia can result in loss of nutrient supply to the affected area. To determine if soluble factors from SB623 cells and MSCs have restorative effects on nutrient-deprived endothelial cells, human umbilical vein endothelial cells (HUVECs) were cultured in medium depleted of serum and growth factors for 24 hours, then exposed to conditioned medium (CM) from MSCs or SB623 cells. Control cultures remained in serum- and growth factor-depleted medium without addition of CM. Viability and proliferative capacity of the HUVECs were then assessed.

For these experiments, human umbilical vein endothelial cells were passed twice, then $7.5 \times 10^5$ cells were plated in EBM-2/EGGS medium (Endothelial Basal Medium-2/Endothelial Cell Growth Supplements; Lonza, Walkersville, Md.) on T-75 flaSks coated with 0.1% gelatin and cultured for 24 hours. The FILIVEC monolayers were rinsed twice with warns PBS and incubated with 12 ml of fresh EBM-2 medium overnight at 37° C., 5% $CO_2$. Effects of CM were then assessed by withdrawing 6 ml of medium from each flask, and replacing it with 6 ml fresh OptiMEM (control), 6 ml MSC conditioned medium, or 6 ml SB623 cell conditioned medium (conditioned media prepared as described in Example 1). After 7 days, non-adherent and adherent cells were collected, centrifuged at 1400 rpm for 5 min, and divided into three fractions for subsequent staining analyses (PI, Bcl-2 and Ki67).

Figure 1:
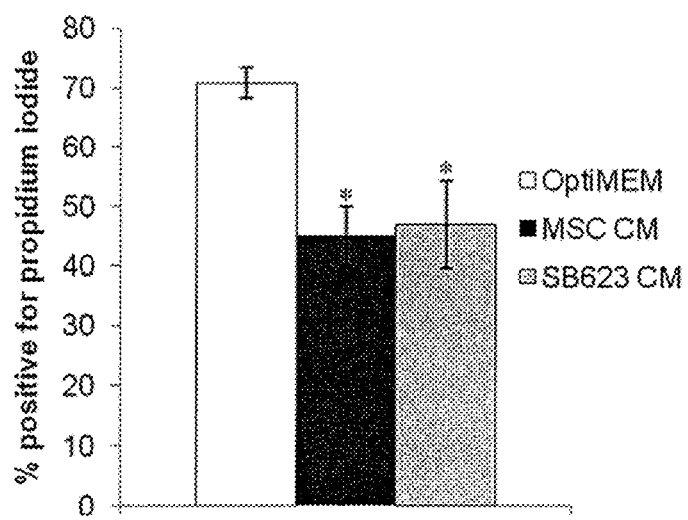
FIG. 1 shows measurements of the fraction of cells permeable to propidium iodide in cultures of HUVECs that have been starved for semm and growth factors. Left-most bar shows results obtained from control serum/growth factor-starved HUVECs; center bar shows results for serum/growth factor-starved HUVECs cultured for seven days in the presence of conditioned medium from MSCs, and the right-most bar shows results for serum/growth factor-starved HUVECs cultured for seven days in the presence of conditioned medium from SB623 cells. Values shown are mean±SD for three separate donors of MSCs and SB623 cells; * indicates $p<0.05$ compared to control group.

To quantify cell death, cells were stained with propidium iodide (PI), since dead cells are permeable to PI. Cells were stained with 5 ug/ml PI for 30 min at room temperature, and, flow cytometry acquisition and analysis were conducted using the FL-2 logarithmic channel of a BD FACSCalibur CellQuest program (BD Biosciences, San Jose, Calif.). For this assay, 3 different human donor pairs were tested. The results are shown in FIG. 1. In control HUVEC cultures maintained in nutrient-deprived medium for 7 days, more than 70% of the cells were positive for propidium iodide staining. Addition of either SB623- or MSC-conditioned medium significantly reduced the percentage of propidium iodide positive cells (p<0.05).

These results indicate that both MSC conditioned medium and SB623 cell conditioned medium significantly reduced death of endothelial cells (i.e., reduced the number of propidium iodide-positive HUVECs) resulting from serum and growth factor starvation.

Bcl-2 is an anti-apoptotic protein originally identified as being overexpressed in certain B-cell lymphomas. Accordingly, the fraction of cells expressing the Bcl-2 protein was measured in serumigrowth factor-starved HUVECs as an indicator of their apoptotic potential. For Bcl-2 measurement, cells were fixed in 4% parafonnaldehyde and permeabilized with 0.1% Triton-X100 for one hour. Following permeabilization, cells were stained for one hour, on ice, with fluorescein-conjugated anti-Bcl-2 antibody, then samples were washed, acquired, and analyzed on the FL-1 channel of a BD FACSCalibur. Cells exposed to fluorescein-conjugated IgG were used as a negative control. For these assays, 3 different human donor pairs were tested.

Figure 2:
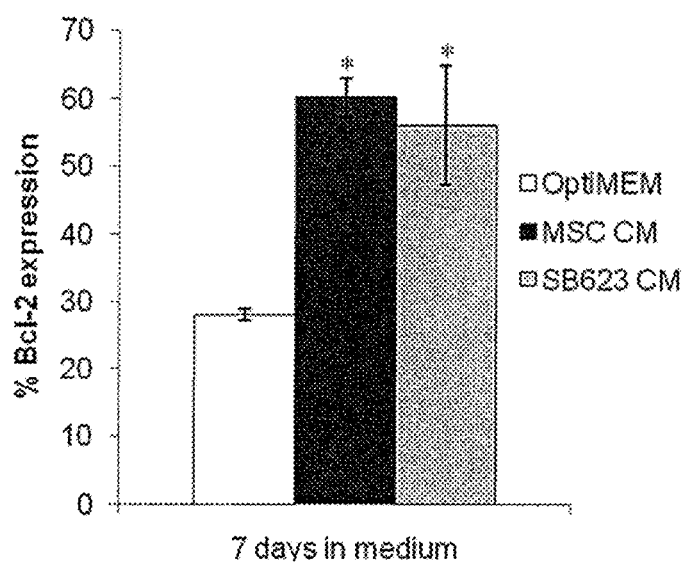
FIG. 2 shows measurement of the fraction of cells expressing Bcl-2 in cultures of HUNTE.Cs that have been starved for serum and growth factors. Left-most bar shows results obtained from control serum/growth factor-starved HUVECs; center bar shows results for serum/growth factor-starved HUVECs. cultured for seven days in the presence of conditioned medium from MSCs, and the right-most bar shows results for serum/growth factor-starved HUVECs cultured for seven days in the presence of conditioned medium from SB623 cells. Results were obtained by measuring fluorescence of cells stained with a fluorescein-conjugated anti-Bcl-2 antibody and subtracting fluorescence of cells exposed to fluorescein-conjugated IgG. Values shown are mean±SD for three separate donors of MSCs and SB623 cells; * indicates $p<0.05$ compared to control group.

The results, shown in FIG. 2, indicate that presence of either MSC conditioned medium or SB623 cell conditioned medium significantly increased the fraction of Bcl-2-positive cells in cultures of serum-starved endothelial cells.

The fact that conditioned medium from MSCs or from SB623 cells decreased the number of dead (PI-positive) cells and increased of the number of cells expressing the anti-apoptotic Bcl-2 protein shows that both MSCs and SB623 cells secrete factors that enhance endothelial cell survival.

Example 3

Effect of SB623 Cell-Secreted Factors on HUVEC Proliferation

Ki67 is a protein present in cells exiting from the G0 (quiescent) phase of the cell cycle; therefore Ki67 levels can be used as a measure of cell proliferation. The fraction of cells expressmg Ki67 protein was measured in HUVECs that had been starved for serum and growth factors, then cultured with conditioned medium from either MSCs or SB623 cells.

For Ki67 measurement, HUVECs were cultured and exposed to CM as described in Example 2. Cells were fixed in 4% paraformaldehyde and permeabilized with 0.1% Triton-X100 for one hour. Following permeabilization, cells were stained for one hour on ice with fluorescein-conjugated anti-KI67 antibody, then samples were washed, acquired, and analyzed on the FL-1 channel of a BD FACSCalibur. Cells exposed to fluorescein-conjugated IgG were used as a negative control. For these assays, 3 different human donor pairs were tested.

Figure 3:
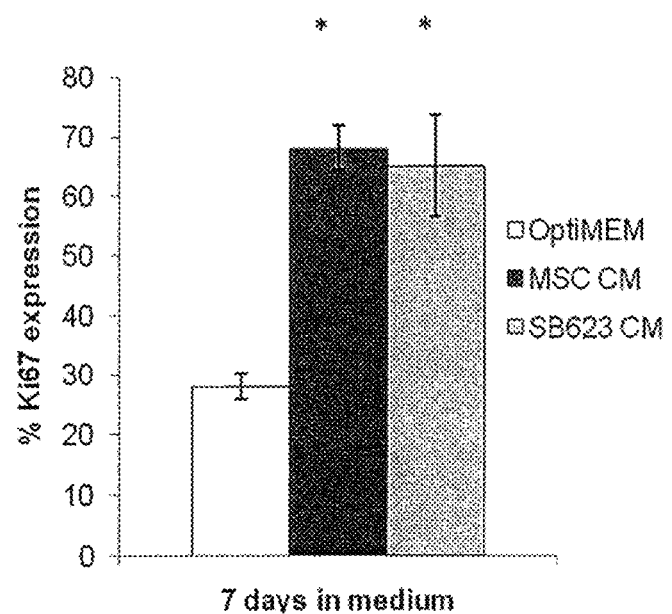
FIG. 3 shows measurement of the fraction of cells expressing Ki67 in cultures of HUVECs that have been starved for serum and growth factors. Left-most bar shows results obtained from control serum/growth factor-starved HUVECs; center bar shows results for serum/growth factor-starved HUVECs cultured for seven days in the presence of conditioned medium from MSCs, and the right-most bar shows results for serum/growth factor-starved HUVECs cultured for seven days in the presence of conditioned medium from SB623 cells. Results were obtained by measuring fluorescence of cells stained with a fluorescein-conjugated anti-Ki67 antibody and subtracting fluorescence of cells exposed to fluorescein-conjugated IgG. Values shown are mean±SD for three separate donors of MSCs and SB623 cells; * indicates $p<0.05$ compared to control group.

FIG. 3 shows that culture of starved HUVECs in the presence of conditioned medium from either MSCs or SB623 cells resulted in an increased fraction of cells expressing Ki67, compared to control HUVECs not exposed to conditioned medium. The fact that conditioned medium from MSCs or from SB623 cells increased the number of cells expressing the proliferation-associated Ki67 protein shows that both MSCs and SB623 cells secrete factors that enhance endothelial cell proliferation.

The results presented in this and the previous example revealed significant increases in survival and proliferation of HUVECs when these endothelial cells were cultured for 7 days with MSC- or SB623 cell-conditioned medium, compared to culture in unconditioned medium (p<0.05).

Example 4

Effect of SB623 Cell-Secreted Factors on Tube Formation by Endothelial Cells

A HUVEC tube formation assay was used to test the ability of MSCs and SB623 cells to elaborate factors that stimulate vessel formation. See, for example, E J Smith & C A Staton, "Tubule formation assays," in *Angiogenesis Assays—A Critical Appraisal of Current Techniques*, (Staton, Lewis & Bicknell, eds.). John Wiley & Sons, Ltd., West Sussex, UK., pp. 65-87, 2006; and Goodwin (2007) *Microvasc. Res.* 74:172-183.

HUVECs were passed five times in E8M-2/ECGS medium, then transferred to alpha-MEM/0.5%1 BS/2 mM glutamine/pen-strep, at a density of $1 \times 10^5$ cells ml. After 24 hours, HTIVECs were harvested using 0.25% trypsin-EDTA, rinsed, and resuspended in α-MEMS2mM glutamine/pen-strep at a density of $1 \times 10^5$ cells/ml. A mixture of 75 ul of HUVECs plus 75 ul of either MSC- or SB623-conditioned medium (Example 1), or 75 ul OptiMEM medium as a negative control, was added to each well of a 96-well plate that had been pre-treated by adding 50 ul of Reduced Growth Factor (RGF)-basement gel (Invitrogen, Carslsbad, Calif.) per well and incubating the plates at 37° C. for 45 minutes. For this assay, MSCs were obtained from 3 different human donors, and a portion of the MSCs from each donor were converted to SB623 cells.

Figure 4:
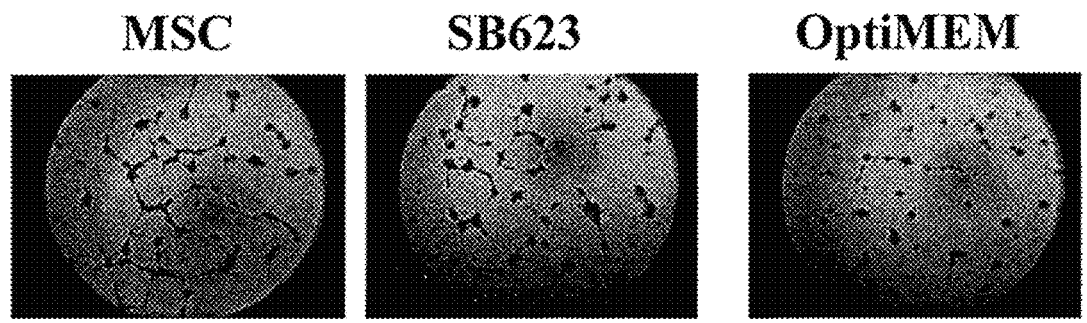
FIG. 4 shows phase-contrast photomicrogaphs of HUVECs following culture for 16 hours in conditioned media from MSCs or SB623 cells. The left-most photograph shows cells cultured in conditioned medium from MSCs; the center photograph shows cells cultured in conditioned medium from SB623 cells; and the right-most photograph shows cells cultured in commercial culture medium without added conditioned medium.
Figure 5:
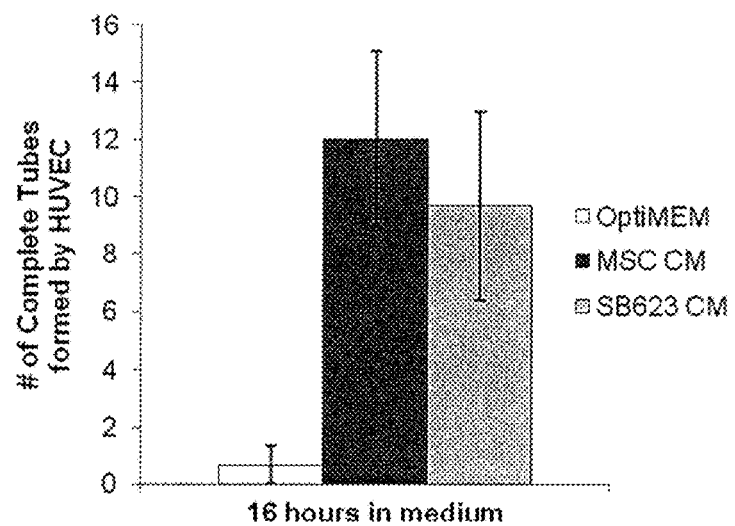
FIG. 5 shows measurement of the effect of conditioned medium on tube formation by HUVECs. Left-most bar shows results obtained from control serum/growth factor-starved HUVECs; center bar shows results for senimigrowth factor-starved HUVECs cultured for 16 hours in the presence of conditioned medium from MSCs, and the right-most bar shows results for senimigrowth factor-starved HUVECs cultured for 16 hours in the presence of conditioned medium from SB623 cells. Values shown are mean+SEM for three separate donors of MSCs and SB623 cells.

After 16 hours, the cultures were examined by phase contrast microscopy and photographed. The number of complete tubes (formed by contiguous cells) was quantified by an experimenter blinded to the group. A photograph showing results from one of the three donors is shown in FIG. 4. The results of assays using MSCs and SB623 cells from all three donors, summarized in FIG. 5, indicate that tube formation is strongly enhanced by conditioned medium from either MSCs or SB623 cells. Thus, MSCs and SB623 cells secrete factors that promote vasculogenesis.

Example 5

Effect of SB623 Cell-Secreted Factors on Vessel Outgrowth and Branching

Restoration of vasculature after ischemic injury requires that surviving endothelial cells receive signals that prompt their migration and invasion. Such signals may arise from vascular smooth muscle cells, monocytes, and/or macrophages, among others. To test for secretion of factors involved in vessel sprouting and branching, the aortic ring assay was used. See, for example, Nicosia & Ottinetti (1990) *Lab. Invest.* 63:115-122 and Nicosia (2009) *J. Cell. Mol. Med.* 13:4113-4136.

For preparation of aortic rings, adult Sprague-Dawley rats were euthanized prior to dissection. After clamping off its two ends, the aorta was removed and placed in ice-cold α-MEM/pen-strep medium prior to removal of the external adipose layer. Adipose-free aorta was rinsed twice with ice-cold EBM-2/pen-strep medium before being sectioned into rings of 1.0 mm thickness. The aortic rings were then transferred to plates containing EBM-2/pen-strep medium and incubated at 37° C., 5% $CO_2$ for 6 days, with the medium replaced with fresh EBM-2/pen-strep medium on day 3, to deplete any endogenous rat angiogenic factors. At that point, the medium was replaced with alpha-MEM/pen-strep medium and culture was continued for 24 hours.

On day 0 of the aortic ring assay (seven days after beginning of culture), 50 µl of reduced growth factor (RGF) basement gel was deposited per well of a 24-well plate. An individual aortic ring was placed in the middle of each gel-coated well and overlaid with an additional 25 µl of RGF-basement gel. After allowing 30 minutes at 37° C./5% $CO_2$ for solidification of the gel, 500 µl of α-MEM/2 mM glutamine/pen-strep was added to each well and incubation was continued for an additional 30 minutes. Then, 500 ul of either MSC- or SB623-derived conditioned medium (Example 1) was added. As a negative control, 500 µl of OptiMEM medium was used in place of conditioned medium.

To assess the angiogenic activity of MSC- and SB623-derived factors, phase contrast photographs were taken on Day 10, and results were quantified by an experimenter blinded to the goup, by counting vessel outgrowth and branching. Growth of new vessels was quantitated by measuring the number of vessels growing out from the ring; and vessel branching was quantitated by measuring the number of branchpoints present in vessels growing out from the aortic ring. For this assay, 7 different human donor pairs were tested.

Figure 6A:
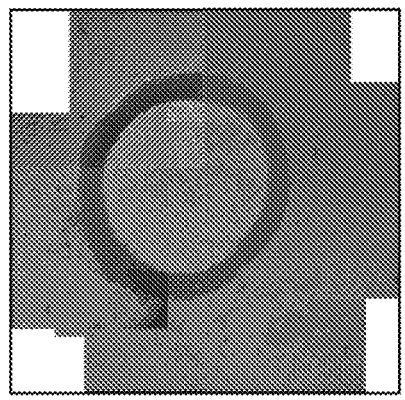
FIGS. 6A-6C show photographs of aortic rings after culture for 10 days in unconditioned medium (A), MSC conditioned medium (B), or SB623 cell conditioned medium (C).
Figure 6B:
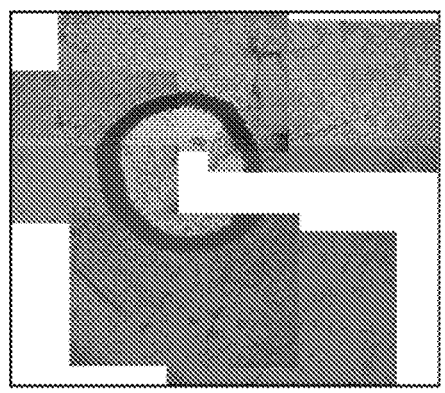
Figure 6C:
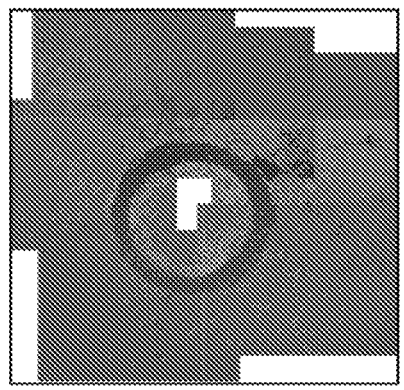
Figure 7A:
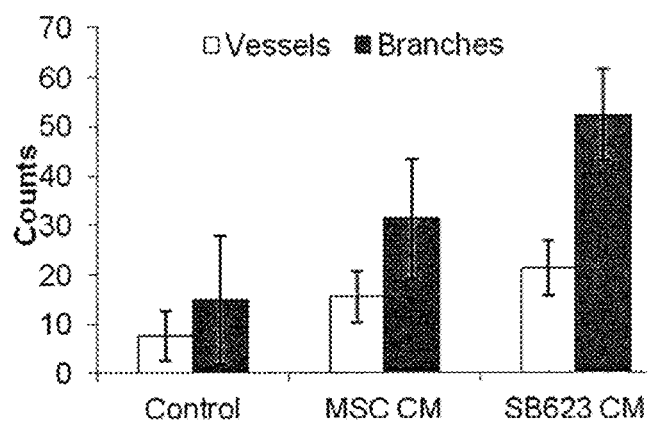
FIGS. 7A and 7B show measurements of vessel sprouting and branching in an aortic ring assay.
Figure 7B:
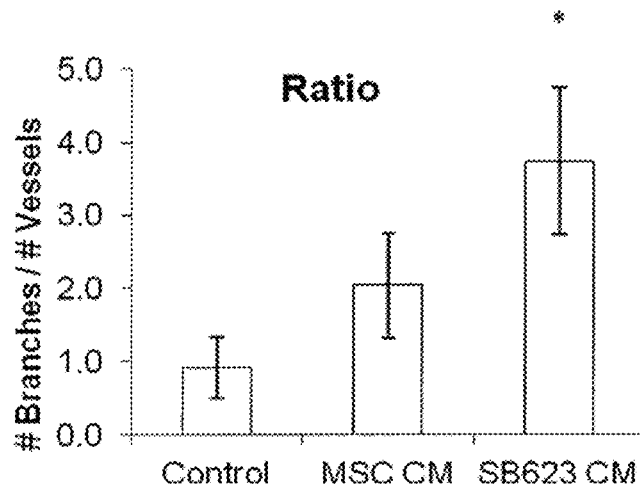

Representative results from Day 10 samples are shown in FIG. 6, and results from seven sets of 10-day cultures are summarized and quantitated in FIG. 7. FIG. 7A shows that conditioned medium from both MSCs and SB623 cells stimulated an increase in the number of newly-sprouted vessels and in the degree of branching, compared to control aortic rings. Moreover, significant increases in vessel branching were observed in rings cultured in SB623 cell-conditioned medium (FIG. 6C, FIG. 7A), compared with either rings cultured in MSC-conditioned medium (FIG. 6B, FIG. 7A) or rings cultured in unconditioned medium (FIG. 6A, FIG. 7A). These results indicate that MSCs and SB623 cells secrete factors that enhance vessel sprouting and vessel branching. In particular, SB623 cells secrete factors that greatly enhance vessel branching (see FIG. 7B).

The data presented the foregoing examples indicate that SB623 cell-secreted soluble factors promote several aspects of angiogenesis, which contribute to recovery in the injured brain.

Example 6

Statistics

For each experiment (which included 3-4 wells/group), a mean value was obtained for: (1) the treatment condition for each cell type (either MSC- or SB623 cell-derived conditioned medium; one value per human donor tested) and (2) the untreated group (one value for each round of testing). For statistical comparison (SigmaStat, SystatSoftware, Chicago, Ill.) each of these values were used and comparisons were made using one way ANOVA between the following groups (1) Control (unconditioned medium: n=3), (2) MSC-conditioned medium (n=3-5): and (3) SB623 cell-conditioned medium (n=3-5). Additional pair-wise comparisons were made using Tukey's test. An alpha value of 0.05 was used to determine whether the means were significantly different.

Example 7

Identification of Angiogenic Factors Secreted by MSCs and SB623 Cells

The levels of certain cytokines and trophic factors in conditioned medium from MSCs and SB623 cells were measured. To obtain conditioned medium, MSCs or SB623 cells were cultured in growth medium to ~90% confluence (~15,000 cells/cm$^2$), at which point medium was removed, the cells were rinsed in PBS, and Opti-MEM® medium (Invitrogen, Carlsbad, Calif.) was added to give a concentration of ~150,000 cells/ml. The conditioned medium was collected 72 hours later and assayed using a Quantibody® Human Angiogenesis Array 1 (RayBiotech, Norcross, Ga.) according to the manufacturer's instructions. For each source of MSCs a portion of the cells were cultured directly as MSCs and a portion were converted to SB623 cells. Thus, a culture of MSCs from a particular donor and a culture of SB623 cells made from those MSCs, are referred to as a matched "donor pair." In this experiment, four donor pairs were assayed. Results, expressed as protein concentration, were normalized to the number of cells present in the culture when the conditioned medium was collected. FIG. 8 shows results, by donor, for angiogenin, ANG-2, HB-EGF and PlGF. FIG. 9 shows results for these four factors, and six others, also by donor, and highlights the large amounts of VEGF produced by MSCs and SB623 cells.

Table 1 shows protein levels averaged among the four donor pairs for the ten factors tested. Although levels of trophic factors secreted were variable among the different donors (as shown, for example, in FIGS. 8 and 9), levels of four of the factors (angiogenin, angiopoietin-2, HB-EGF and PlGF) were consistently different between MSCs and SB623 cells. Angiogenin, ANG-2 and HB-EGF were more highly expressed by SB623 cells, while higher concentrations of PlGF were produced by MSCs.

TABLE 1

Levels of Angiogenic trophic factors
in conditioned medium from MSCs and SB623 Cells

| | MSCs | | SB623 Cells | |
|---|---|---|---|---|
| FACTOR | AVG | SD | AVG | SD |
| Angiogenin | 741 | 178 | 985 | 271 |
| ANG-2 | 540 | 252 | 641 | 275 |
| EGF | — | n/a | — | n/a |
| bFGF | 53 | 7 | 40 | 17 |
| HB-EGF | 205 | 162 | 282 | 228 |
| HGF | 123 | 55 | 143 | 75 |
| Leptin | 397 | 226 | 437 | 213 |
| PDGF-BB | 18 | 22 | 16 | 18 |
| PlGF | 300 | 178 | 171 | 85 |
| VEGF | 30,503 | 9229 | 38,119 | 8692 |

Abbreviations are as follows.
ANG-2: angiopoietin-2;
EGF: epidermal growth factor;
bFGF: basic fibroblast growth factor/fibroblast growth factor 2;
HB-EGF: heparin-binding epidermal growth factor-like growth factor;
HGF: hepatocyte growth factor;
PDGF-BB: platelet-derived growth factor-BB;
PlGF: placental growth factor;
VEGF: vascular endothelial growth factor. Numbers refer to cytokine levels expressed as pg/ml/$10^6$ cells.
"AVG" refers to the average value from 4 sources of MSCs and 4 sources of SB623 cells from which conditioned medium was obtained;
"SD" refers to standard deviation.
"—" indicates that levels, if any, were below the limit of detection in the assay;
"n/a" indicates "not applicable"

Example 8

Effect of an Inhibitor of VEGF Signaling on HUVEC Viability and Proliferation

In light of the large amounts of VEGF secreted by both MSCs and SB623 cells, the contribution of VEGF to the pro-angiogenic activities of MSC- and SB623-conditioned media was tested using an inhibitor of VEGF signaling. SU5416 (VEGFR2 kinase inhibitor III, EMD Millipore, Billerica, Mass.) blocks downstream signaling by VEGF receptor 2 (Flk-1) and, to a lesser extent, by VEGF receptor 1 (Flt-1) and other receptor tyrosine kinases, thereby inhibiting angiogenesis.

HUVEC viability assays (propidium iodide uptake and Bcl-2 expression) were conducted as described in Example 2 on two batches of SB623 cell-conditioned medium, in the presence and absence of 50 nM SU5416 except that cells were cultured for live days, instead of seven, before assay. The inhibitor was added to cultures 30 minutes before addition of CM. Since higher concentrations of SU5416 can inhibit receptor tyrosine kinases other than VEGFR2, this SU5416 concentration was chosen so that VEGFR2 signaling (but not signaling by, e.g., PDGF receptor, EGF receptors, or Flt3) was inhibited. The results, shown in FIGS. 10A and 10B, indicate that more cells take up PI (FIG. 10A) and fewer cells express the anti-apoptotic Bcl-2 protein (FIG. 10B) when HUVECs are cultured in SB623 conditioned medium and SU5416, than when they are cultured in SB623 cell-conditioned medium alone. Thus, inhibition of VEGF receptor activity partially reduces the positive effect of SB623 cell-conditioned medium on viability of HUVECs, pointing to a role of the VEGF protein in these effects.

The effect of the VEGF receptor inhibitor on stimulation of HUVEC proliferation by SB623 cell factors was also assessed. Assays for expression of Ki67 were conducted as described in Example 3, except that 50 nM SU5416 was added to cultures 30 minutes before addition of conditioned medium, and cells were cultured for five days, instead of seven, before assay. The results, shown in FIG. 11 and averaged from two donors, indicate that the enhancement of HUVEC proliferation observed in the presence of conditioned medium from SB623 cells was partially reversed by inhibition of VEGFR2.

These results point to a role for VEGF, in addition to other SB623 cell-derived factors, in the pro-survival and pro-proliferative activity of MSC and SB623 cell conditioned media.

Example 9

Effect of an Inhibitor of VEGF Signaling on Tube Formation by Human Umbilical Vein Endothelial Cells (HUVECs)

HUVEC tube formation assays with conditioned medium from MSCs and SB623 cells were conducted as described in Example 4, in the presence and absence of the VFGF2 receptor inhibitor SU5416. Cells cultured in the absence of conditioned medium were used as negative controls; and cells cultured in the presence of VEGF (10 ng/ml were used as positive controls. The results, shown in FIG. 12, indicate that VEGF, MSC-conditioned medium and SB623 cell-conditioned medium all promote tube formation; while the VEGFR2 inhibitor SU5416 reduces the stimulation of tube formation by all of these agents.

Quantitation of tube formation was conducted, as described in Example 4, for HUVECs exposed to SB623 cell conditioned medium in the presence and absence of SU5416, at 16 and 40 hours after plating. The results, shown in FIG. 13, indicate that, at both time points, inhibition of VEGFR2 completely reversed the positive effect of CM on tube formation.

Example 10

Effect of an Inhibitor of VEGF Signaling on Vessel Outgrowth and Branching in an Aortic Ring Assay Aortic ring angiogenesis assays were conducted as described in Example 5 on one batch of SB623 cell-conditioned medium, in the presence and absence of 50 nM SU5416. The inhibitor was added to cultures 30 minutes before addition of CM and rings were assayed after 10 days of culture. The results indicate that the vessel outgrowth and branching resulting from culture of aortic rings in SB623 cell-conditioned medium (FIG. 14, compare left and center panels) was reduced in the presence of the VEGF receptor inhibitor SU5416 (FIG. 14, compare center and right panels). These results provide fu Cher evidence for the role of VEGF in the pro-angiogenic activities of SB623 cell-conditioned medium.

The results obtained using a VEGF receptor inhibitor (described above), while confirming the importance of VEGF to these processes (particularly tube formation, vessel outgrowth and vessel branching) do not rule out the participation of additional factors (other than VEGF) in the pro-angiogenic activities of MSC- and SB623 cell-conditioned media.

What is claimed is:

1. A method for treating an ischemic disorder in a subject, wherein the ischemic disorder occurs outside the central nervous system, the method comprising:
    administering, to a site of ischemic disorder in the subject that is outside the central nervous system, a therapeutically effective amount of cells, wherein the cells are made by a method comprising:
    (a) providing a culture of mesenchymal stem cells,
    (b) contacting the cell culture of step (a) with a polynucleotide comprising sequences encoding a Notch intracellular domain (NICD) wherein said polynucleotide does not encode a full-length Notch protein,
    (c) selecting cells that comprise the polynucleotide of step (b), and
    (d) further culturing the selected cells of step (c) in the absence of selection and in the absence of trophic factors;
    wherein the cells produce angiogenin, angiopoietin-2 (ANG-2) and heparin-binding epidermal growth factor-like growth factor (HB-EGF) at higher levels than do the mesenchymal stem cells of step (a).

2. The method of claim 1, wherein the ischemic disorder is selected from the group consisting of cardiac ischemia, ischemia of the bowel, ischemia of the limb, cutaneous ischemia, retinal ischemia and cerebral palsy.

3. The method of claim 2, wherein the ischemia of the bowel is ischemic colitis or mesenteric ischemia.

4. The method of claim 1, wherein the cells produce one or more additional angiogenic factors selected from the group consisting of basic fibroblast growth factor, leptin, platelet-derived growth factor-BB, hepatocyte growth factor, vascular endothelial growth factor and placental growth factor.

5. The method of claim 1, wherein administration results in augmentation of blood vessel sprouting.

6. The method of claim 1, wherein administration results in prevention of endothelial cell death.

7. The method of claim 1, wherein administration results in enhancement of endothelial cell survival.

8. The method of claim 1, wherein administration results in stimulation of endothelial cell proliferation.

9. The method of claim 1, wherein administration results in enhancement of vessel branching.

10. A combination for use in treating an ischemic disorder in a subject, wherein the ischemic disorder occurs outside the central nervous system, wherein the combination comprises:
    (a) a first pro-angiogenic agent comprising cells made by a method comprising:
        (i) providing a culture of mesenchymal stem cells,
        (ii) contacting the cell culture of step (i) with a polynucleotide comprising sequences encoding a Notch intracellular domain (NICD) wherein said polynucleotide does not encode a full-length Notch protein,
        (iii) selecting cells that comprise the polynucleotide of step (ii), and
        (iv) further culturing the selected cells of step (iii) in the absence of selection and in the absence of trophic factors;
    wherein the cells produce angiogenin, angiopoietin-2 (ANG-2) and heparin-binding epidermal growth factor-like growth factor (HB-EGF) at higher levels than do the mesenchymal stem cells of step (i); and
    (b) a second pro-angiogenic agent.

11. The combination of claim 10, wherein the second pro-angiogenic agent is a polypeptide.

12. The combination of claim 11, wherein the polypeptide is a transcription factor that activates transcription of a pro-angiogenic protein.

13. The combination of claim 12, wherein the pro-angiogenic protein is vascular endothelial growth factor (VEGF).

14. The combination of claim 13, wherein the transcription factor is a non-naturally-occurring zinc finger protein that activates transcription of the VEGF gene.

15. The combination of claim 10, wherein the second pro-angiogenic agent is a nucleic acid.

16. The combination of claim 15, wherein the nucleic acid encodes a transcription factor that activates transcription of a pro-angiogenic protein.

17. The combination of claim 16, wherein the pro-angiogenic protein is vascular endothelial growth factor (VEGF).

18. The combination of claim 17, wherein the transcription factor is a non-naturally-occurring zinc finger protein that activates transcription of the VEGF gene.

19. A method for use in treating an ischemic disorder in a subject, wherein the ischemic disorder occurs outside the central nervous system, the method comprising administering to the subject a therapeutically effective amount of the combination of claim 10.

20. The method of claim 19, wherein administration results in augmentation of angiogenesis.

21. The method of claim 20, wherein said augmentation of angiogenesis comprises a process selected from the group consisting of one or more of prevention of endothelial cell death, enhancement of endothelial cell survival, stimulation of endothelial cell proliferation, enhancement of blood vessel sprouting and enhancement of blood vessel branching.

* * * * *